US008725419B2

(12) United States Patent
Sayood et al.

(10) Patent No.: US 8,725,419 B2
(45) Date of Patent: May 13, 2014

(54) SYSTEM AND METHOD FOR SEQUENCE DISTANCE MEASURE FOR PHYLOGENETIC TREE CONSTRUCTION

(75) Inventors: Khalid Sayood, Linclon, NE (US); Hasan H. Otu, Boston, MA (US); Steven H. Hinrichs, Omaha, NE (US)

(73) Assignee: NUtech Ventures, Lincoln, NE (US)

( * ) Notice: Subject to any disclaimer, the term of this patent is extended or adjusted under 35 U.S.C. 154(b) by 1891 days.

(21) Appl. No.: 10/561,889

(22) PCT Filed: Jun. 21, 2004

(86) PCT No.: PCT/US2004/019762
§ 371 (c)(1),
(2), (4) Date: Sep. 6, 2006

(87) PCT Pub. No.: WO2004/113505
PCT Pub. Date: Dec. 29, 2004

(65) Prior Publication Data
US 2007/0225918 A1   Sep. 27, 2007

Related U.S. Application Data

(60) Provisional application No. 60/479,668, filed on Jun. 19, 2003.

(51) Int. Cl.
*G01N 33/48* (2006.01)
(52) U.S. Cl.
USPC .......................................................... 702/19
(58) Field of Classification Search
USPC ............................................................ 702/19
See application file for complete search history.

(56) References Cited

U.S. PATENT DOCUMENTS 5,710,916 A * 1/1998 Barbara et al. .................... 1/1
7,080,320 B2 * 7/2006 Ono ............................. 715/264

OTHER PUBLICATIONS

Felsenstein, J. Evolutionary trees from DNA sequences: a maximum likelihood approach. Journal of Molecular Evolution. vol. 17, 1981, pp. 368-376.*
Varre et al. Transformation distances: a family of dissimilarity measures based on movements of segments. Bioinformatics, 1999, vol. 15, pp. 194-202.*
Queen et al. A comprehensive sequence analysis program for the IBM personal computer. Nucleic Acids Research, vol. 12, 1984, pp. 581-599.*
Altschul, Stephen F., et al., Basic Local Alignment Search Tool, J.Mol. Biol. (1990) 215, 403-410.
Sankoff, David, Matching Sequences Under Delection/Insertion Constraints, Proc. Nat. Acad. Sci. USA, vol. 69, No. 1, pp. 4-6, Jan. 1972.
Apostolico et al., "Compression of Biological Sequences by Greedy Off-line Textual Substitution," *Data Compression Conference*, IEEE Computer Society Technical Committee on Computer Communications, 143-152, 2000.
Bally and Hartigan, "Statistical Analysis of Hominoid Molecular Evolution," *Statistical Science*, 2(2):191-210, 1987.
Benedetto, et al., "Language Trees and Zipping," *Physical Review Letters*, 88:048702-1-048702-4, 2002.
Bennett et al., "Information Distance," *IEEE Transactions on Information Theory*, 44, 1407-1423, 1998.
Berbee and Taylor, "Two Ascomycete Classes Based on Fruiting-body Characters and Ribosomal DNA Sequence," *Molecular Biology and Evolution*, 159:278-284, 1992.
Berman et al., "1.375—Approximation algorithm for sorting by reversals," *Technical Report TROI-047*, ECCC, 1-42, 2001.
Boore and Brown, "Big Trees from Little Genomes: Mitochondrial Gene Order as a Phylogenetic Tool," *Curro Opin. Genet. Dev.*, 8:668-674, 1998.
Camin and Sokal, "A Method for Deducing Branching Sequences in Phylogeny," *Evolution*, 19:311-326, 1965.
Cao et al., "Conflict Among Individual Mitochondrial Proteins in Resolving the Phylogeny of Eutherian Orders," *J. Mol. Evol.*, 47:307-322, 1998.
Cao et al., "Phylogenetic Position of Guinea Pigs Revisited," *Mol. Biol. Evol.*, 14:461-461, 1997.
Cavalli-Sforza and Edwards "Phylogenetic Analysis: Models and Estimation Procedures," *Evolution*, 21:550-570, 1967.
Chen et al., "A Compression Algorithm for DNA Sequences and Its Applications in Genome Comparison," *Proceedings of the Fourth Annual International Conference on Computational Molecular Biology*, 107-117, 2000.
Eck et al., "Atlas of Protein Sequence and Structure," *35 National Biomedical Research Foundation*, 161-202, 1966.
Farach et al., "On the Entropy of DNA: Algorithms and Measurements Based on Memory and Rapid Convergence," *In Symposium on Discrete Algorithms*, 48-57, 1995.
Felsenstein and Churchill, "A Hidden Markov Model Approach to Variation Among Sites in Rate of Evolution," *Mol. Bio. Evol.*, 13:93-104, 1996.

(Continued)

*Primary Examiner* — Jerry Lin
(74) *Attorney, Agent, or Firm* — Fish & Richardson P.C.

(57) ABSTRACT

The present invention permits identification of biological materials following recovery of DNA using standard techniques by comparing a mathematical characterization of the unknown sequence with the mathematical characterization of DNA sequences of known genera and species. The clinical identification of infectious organisms is required for accurate diagnosis and selection of antimicrobial therapeutics. The invention allows an ab initio approach with the potential for rapid identification of biological materials of unknown origin. The approach provides for identification and classification of emergent or new organisms without previous phenotypic identification. The technique may also be used in monitoring situations where the need exists for classification of material into broad categories of bacteria which could have an immediate impact on bio-terrorism prevention.

26 Claims, 9 Drawing Sheets

(56) References Cited

OTHER PUBLICATIONS

Felsenstein, "Maximum Likelihood and Minimum-steps Methods for Estimating Evolutionary Trees from Data on Discrete Characters," *Syst. Zool.*, 22:240-249, 1973.

Felsenstein, "Hennig86: A PC-DOS Program for Phylogenetic Analysis," *Cladistics*, 5:163-166, 1989.

Fitch, "Toward Defining the Course of Evolution: Minimum Change for a Specific Tree Topology," *Syst. Zool.*, 35:406-416, 1971.

Fitz-Gibbon et al., "Whole Genome-based Phylogenetic Analysis of Free-living Microorganisms," *Nucleic Acids Res.*, 27:4218-4222, 1999.

Grumbach and Tahi, "A New Challenge for Compression Algorithms: Genetic Sequences," *J. Info. Proc. Man.*, 30:875-866, 1994.

Grumbach and Tahi, "Compression of DNA Sequences," *Data Compression Conference*, IEEE Computer Society Press, 340-350, 1993.

Hannenhalli and Pevzner "Towards a Computational Theory of Genome Rearrangements," *Computer Science Today: Recent Trends and Developments*, 1000:184-202, 1995.

Hannenhalli and Pevzner, "Transforming Cabbage into Turnip: Polynomial Algorithm for Sorting Signed Permutations by Reversals," *JACM*, 46:1-27, 1999.

Henry et al., "Identification of *Aspergillus* Species Using Internal Transcribed Spacer Regions 1 and 2," *Journal of Clinical Microbiology*, 38: 1510-1515, 2000.

Herr et al., "Phylogenetic Analysis of *Lacazia loboi* Places This Previously Uncharacterized Pathogen within the Dimorphic Onygenales," *Journal of Clinical Microbiology*, 39:309-314, 2001.

Huynen et al., "Predicting Protein Function by Genomic Context: Quantitative Evaluation and Qualitative Inferences," *Genome Res.*, 10:1204-1210, 2000.

Jukes and Cantor, *Mammalian Protein Metabolism*, Academic Press, 21-132, 1969.

Kececioglu and Sankoff, "Exact and Approximation Algorithms for Sorting by Reversals, with Application to Genome Rearrangement," *Algorithmica*, 13:180-210, 1995.

Kececioglu and Ravi, "Of Mice and Men: Algorithms for Evolutionary Distances Between Genomes with Translocation," *Proceedings of the 6th ACM-SIAM Symposium*, 604-613, 1995.

Kececioglu and Gusfield, "Reconstructing a History of Recombinations from a Set of Sequences," *Discrete Appl. Math.*, 88:239-260, 1998.

Kimura et al., "A Simple Model for Estimating Evolutionary Rates of Base Substitutions Through Comparative Studies of Nucleotide Sequences," *J. Mol. Evol.*, 16:111-120, 1980.

Kishino and Hasegawa, "Evaluation of the Maximum Likelihood Estimate of the Evolutionary Tree Topologies from DNA Sequence Data, and the Branching Order in Hominoidea," *J. Mol. Evol.*, 29: 170-179, 1989.

Lake et al., "Reconstructing Evolutionary Trees from DNA and Protein Sequences: Paralinear Distances," *Proc. Natl. Acad. Sci.*, 91:1455-1459, 1994.

Lanctot et al, "Estimating DNA Sequence Entropy," *Symposium on Discrete Algorithms*, 409-418, 2000.

Li et al., "An Information-based Sequence Distance and its Application to Whole Mitochondrial Genome Phylogeny," *Bioinformatics*, 17(2):149-154, 2001.

Li and Vitanyi, "Information Distance," *An Introduction to Kolmogorov Complexity and Its Applications*, Springer, 641-650, 1997.

Lin and Gerstein, "Whole-genome Trees Based on the Occurrence of Folds and Orthologs: Implications for Comparing Genomes on Different Levels," *Genome Res.*, 10:808-818, 2000.

Loewenstern and Yianilos, "Significantly Lower Entropy Estimates for Natural DNA Sequences," *J. Comput. Bio.*, 6:125-142, 1999.

Madsen et al., "Parallel Adaptive Radiations in Two Major Clades of Placental Mammals," *Nature*, 409:610-618, 2001.

Milosavljevic, "Discovering Sequence Similarity by the Algorithmic Significance Method," *Intelligent Systems for Molecular Biology*, AAAI Press, 284-291, 1993.

Murphy et al., "Resolution of the Early Placental Mammal Radiation Using Bayesian Phylogenetics," *Science*, 294:2348-2351, 2001.

Reyes et al., "Where do Rodents Fit? Evidence from the Complete Mitochondrial Genome of *Sciurus Vulgaris*," *Mol. Bio. Evol.*, 17:979-983, 2000.

Rivals et al., "Compression and Genetic Sequences Analysis," *Biochimie*, 78:315-322, 1996.

Rivals et al., "Compression and Sequence Comparison," *DIMACS Workshop on Sequence Comparison*, 5 pages, 1994.

Rivals et al., "Detection of Significant Patterns by Compression Algorithms: The Case of Approximate Tandem Repeats in DNA Sequences," *Comput. Appl. Biosci.*, 13:131-136, 1997.

Saitou and Nei, "The Neighbor-joining Method: A New Method for Reconstructing Phylogenetic Trees," *Mol. Biol. Evol.*, 4:406-425, 1987.

Sankoff and Blanchette, "Multiple Genome Rearrangement and Breakpoint Phylogeny," *J. Comput. Biol.*, 5:555-570, 1998.

Sankoff et al., "Gene Order Comparisons for Phylogenetic Inference: Evolution of the Mitochondrial Genome," *Proc. Natl. Acad. Sci.*, 89:6575-6579, 1992.

Sankoff, "Comparative Mapping and Genome Rearrangement," *From Jay Lush to Genomics: Visions for Animal Breeding and Genetics*, pp. 124-134, 1999.

Sankoff, "Genome Rearrangement with Gene Families," *Bioinformatics*, 15:909-917, 1999.

Snel et al., "Genome Evolution: Gene Fusion Versus Gene Fission," *Trends Genet.*, 16:9-11, 2000.

Snel et al., "Genome Phylogeny Based on Gene Content," *Nat. Genet.*, 21:108-110, 1999.

Snel et al., "Genomes in Flux: the Evolution of Archaeal and Proteobacterial Gene Content," *Genome Res.*, 12:17-25, 2002.

Tekaia et al., "The Genomic Tree as Revealed from Whole Proteome Comparisons," *Genome Res.*, 9:550-557, 1999.

Thompson et al., "CLUSTAL W: Improving the Sensitivity of Progressive Multiple Sequence Alignment through Sequence Weighting, Positions-specific Gap Penalties and Weight Matrix Choice," *Nucleic Acids Res.*, 22:4673-4680, 1994.

Yokoyama et al., "Identification and Phylogenetic Relationship of the Most Common Pathogenic *Candida* Species Inferred from Mitochondrial Cytochrome b Gene Sequences," *Journal of Clinical Microbiology*, 38: 4503-4510, 2000.

Ziv et al., "A Measure of Relative Entropy Between Individual Sequences with Application to Universal Classification," *IEEE T. Infonn. Theory*, 39:1270-1279, 1993.

Ziv et al., "A Universal Algorithm for Sequential Data Compression," *IEEE T. Inform. Theory*, 23: 337-343, 1977.

\* cited by examiner

| 1 | NOTHING | A | A |
| 2 | NOTHING | T | A,T |
| 3 | NOTHING | G | A,T,G |
| 4 | TG | A | A,T,G,TGA |
| 5 | ATG | | A,T,G,TGA, ATG |

SEQUENCE LISTING

```
<160> NUMBER OF SEQ ID NOS: 6

<210> SEQ ID NO 1
<211> LENGTH: 10
<212> TYPE: DNA
<213> ORGANISM: Artificial Sequence
<220> FEATURE:
<223> OTHER INFORMATION: oligonucleotide

<400> SEQUENCE: 1
aacgtcgtcg                                                          10
```

```
<210> SEQ ID NO 2
<211> LENGTH: 11
<212> TYPE: DNA
<213> ORGANISM: Artificial Sequence
<220> FEATURE:
<223> OTHER INFORMATION: oligonucleotide

<400> SEQUENCE: 2
aacgtacatt g                                                            11

<210> SEQ ID NO 3
<211> LENGTH: 12
<212> TYPE: DNA
<213> ORGANISM: Artificial Sequence
<220> FEATURE:
<223> OTHER INFORMATION: oligonucleotide

<400> SEQUENCE: 3
ctagggactt at                                                           12

<210> SEQ ID NO 4
<211> LENGTH: 11
<212> TYPE: DNA
<213> ORGANISM: Artificial Sequence
<220> FEATURE:
<223> OTHER INFORMATION: oligonucleotide

<400> SEQUENCE: 4
acggtcacca a                                                            11

<210> SEQ ID NO 5
<211> LENGTH: 23
<212> TYPE: DNA
<213> ORGANISM: Artificial Sequence
<220> FEATURE:
<223> OTHER INFORMATION: oligonucleotide

<400> SEQUENCE: 5
aacgtaccat tgacggtcac caa                                               23

<210> SEQ ID NO 6
<211> LENGTH: 23
<212> TYPE: DNA
<213> ORGANISM: Artificial Sequence
<220> FEATURE:
<223> OTHER INFORMATION: oligonucleotide

<400> SEQUENCE: 6
ctagggactt atacggtcac caa                                               23
```

SYSTEM AND METHOD FOR SEQUENCE DISTANCE MEASURE FOR PHYLOGENETIC TREE CONSTRUCTION

CROSS REFERENCE TO RELATED APPLICATIONS

This application is the National Stage of International Application No. PCT/US04/19762 filed Jun. 21, 2004, which claims priority to U.S. Provisional patent Application 60/479,668 filed Jun. 19, 2003. The contents of the above applications are incorporated by reference in their entireties.

BACKGROUND OF THE INVENTION

Phylogenetic analysis using biological sequences can be divided into two groups. The algorithms in the first group calculate a matrix representing the distance between each pair of sequences and then transform this matrix into a tree. In the second type of approach, instead of building a tree, the tree that can best explain the observed sequences under the evolutionary assumption is found by evaluating the fitness of different topologies.

Some of the approaches in the first category utilize various distance measures which use different models of nucleotide substitution or amino acid replacement. [2] [28] [30] [32] [34] The second category can further be divided into two groups based on the optimality criterion used in tree evaluation: parsimony [8] [11] [13] [19] and maximum likelihood methods [15] [16] [18].

All of these methods require a multiple alignment of the sequences and assume some sort of an evolutionary model. In addition to problems in multiple alignment (computational complexity and the inherent ambiguity of the alignment cost criteria) and evolutionary models (they are usually controversial), these methods become insufficient for phylogenies using complete genomes. Multiple alignment becomes misleading due to gene rearrangements, inversion, transposition and translocation at the substring level, unequal length of sequences, etc. and statistical evolutionary models are yet to be suggested for complete genomes. On the other hand, whole genome-based phylogenetic analyses are appealing because single gene sequences generally do not possess enough information to construct an evolutionary history of organisms. Factors such as different rates of evolution and horizontal gene transfer make phylogenetic analysis of species using single gene sequences difficult.

To overcome these problems, Sankoff et al. (1992) [51] defined an evolutionary edit distance as the number of inversions, transpositions and deletions or insertions required to change the gene order of one genome into another. Similar distance measures using rearrangement, recombination, breakpoint, comparative mapping and gene order have been extensively studied for applications to genome-based phylogeny. [6] [7] [23] [24] [29] [30] [31] [48] [49] [50] However, these approaches are computationally expensive and do not produce correct results on events such as non-contiguous copies of a gene on the genome or non-decisive gene order (as in mammalian mtDNA where genes are in the same order).

Gene content was proposed by Snel et al. (1999) [52] as a distance measure in genome phylogeny where the similarity between two species is defined as the number of genes they have in common divided by their total number of genes. The general idea is further extended to identify evolutionary history and protein functionality. [20] [27] [38] [53] [54] Lin and Gerstein (2000) [38] constructed phylogenetic trees based on the occurrence of particular molecular features: presence or absence of either folds or orthologs throughout the whole genome. Takaia et al. (1999) [55] used whole proteome comparisons in deriving genome phylogeny, taking into account the overall similarity and the predicted gene product content of each organism. However, such methods fail to work when the gene content of the organisms are very similar (again as is the case with mammalian mtDNA where the genomes contain exactly the same genes).

In the early 1990s, various data compression approaches were applied to the analysis of genetic sequences. [14] [21] [22] [41] [45] Data compression algorithms function by identifying the regularities in the given sequence, and in case of DNA sequences, these regularities would have biological implications. Grumbach and Tahi (1993, 1994) [21] [22] coded exact repeats and palindromes in DNA along the lines of Lempel-Ziv (LZ) compression scheme [59] and used an arithmetic coder of order 2 when such structures are lacking. Rivals et al. (1994, 1996) [44] [45] compressed the repeats which introduced a significant compression gain and introduced a second compressor which made use of approximate tandem repeats. Rivals et al. (1997) [46] also introduced a compression algorithm which locates and utilizes approximate tandem repeats of short motifs. Some of the later approaches include Loewenstern and Yianilos, 1999; Lanctot et al., 2000; Apostolico and Lonardi, 2000. [1] [35] [39] Grumbach and Tahi (1994) noted that the compression rate obtained by compressing sequence S using sequence Q would hint at some sort of a distance between the two sequences. [22] Although the proposed distance was not mathematically valid and had some other problems, it applied data compression to phylogeny construction.

Varre et al. (1999) [57] defined a transformation distance where sequence S is built from sequence Q by segment-copy, -reverse-copy and -insertion. The total distance is the Minimum Description Length among all possible operations that convert S into Q. This distance, as the one provided by Grumbach and Tahi (1994) [22], is asymmetric. Chen et al. (2000) [12] described a compression algorithm (GenCompress) based on approximate repeats in DNA sequences. The program is then used to approximate the distance proposed therein and the distance proposed by Li et al. (2001). [36] Ziv and Merhav (1993) [4] and Bennett et al. (1998) [6] provide a detailed analysis of information distance in statistical and algorithmic settings.

The distance proposed by Chen et al. (2000) and Li et al. (2001) is $1-[K(S)-K(S|Q)]/K(SQ)$, where $K(S)$ is the Kolmogorov complexity of S, $K(S|Q)$ is the conditional Kolmogorov complexity of S given Q and $K(SQ)$ is the Kolmogorov complexity of the sequence S concatenated with Q. $K(S|Q)$ is the shortest program that outputs S when the input is Q on a universal computer and $K(S)$ is $K(S|\_)$, where _ is the empty string. [12] [33] Kolmogorov complexity is an algorithmic measure of information (Li and Vitanyi, 1997) but it is a theoretical limit and generally can only be approximated. [37] In calculating the aforementioned distance, $K(MQ)$ is approximated by the length of the compressed result of S (using the program GenCompress) given Q.

Benedetto et al. (2002) [3] used a similar idea where relative complexity between sequences S and Q is approximated as it is done by Chen et al. (2000) [12], this time using gzip. However, both gzip and GenCompress are complicated programs, composed of multiple complex steps (algorithms to reduce search space, find exact/approximate matches, perform entropy coding, etc.), which would affect the final result on the complexity estimates in an ambiguous way. Therefore the properties of the distance measures based on Kolmogorov complexity (implicitly or explicitly) would not necessarily hold for these approximations depending on the performance of the compression algorithms on certain sequences.

Methods that rely on the compressibility of a sequence using a compression package have an inherent flaw as these are complicated programs, composed of multiple complex steps (algorithms to reduce search space, find exact/approximate matches, perform entropy coding, etc.), which would affect the final result on the complexity estimates in an ambiguous way. Therefore the properties of the distance measure based on Kolmogorov complexity (implicitly or explicitly) would not necessarily hold for these approximations and the resulting distance may be misleading depending on the performance of the compression algorithms on certain sequences.

Traditional methods are based on phenotypic identification of organisms following the use of culture techniques. Clinical microbiology is currently undergoing a major transition to the use of molecular approaches. However, molecular approaches require the operator to select from among a list of probes or amplification primers for the identification process to proceed. In other words, the operator must have some predetermined idea as to the name or nature of the organism to be identified.

What would be beneficial is a system and method for phylogeny construction that does not require multiple alignment and is fully automatic. It would also be beneficial not to have to use approximations and assumptions in calculating the distance between sequences.

SUMMARY OF THE INVENTION

In one embodiment, the present invention permits identification of biological materials following recovery of DNA using standard techniques by comparing a mathematical characterization of the unknown sequence with the mathematical characterization of DNA sequences of known genera and species. The clinical identification of infectious organisms is required for accurate diagnosis and selection of antimicrobial therapeutics.

In another embodiment, this invention allows an ab initio approach with the potential for rapid identification of biological materials of unknown origin. The approach provides for identification and classification of emergent or new organisms without previous phenotypic identification. The technique may also be used in monitoring situations where the need exists for classification of material into broad categories of bacteria, such as Bacillus versus Franciscella, which could have an immediate impact on bio-terrorism prevention.

Unequal sequence length or the relatively different positioning of similar regions between sequences (such as different gene order in genomes) is not problematic as the proposed method handles both cases naturally. The proposed metrics utilize the entire information contained in the sequences and require no human intervention.

DESCRIPTION OF INVENTION

Figure 1A:
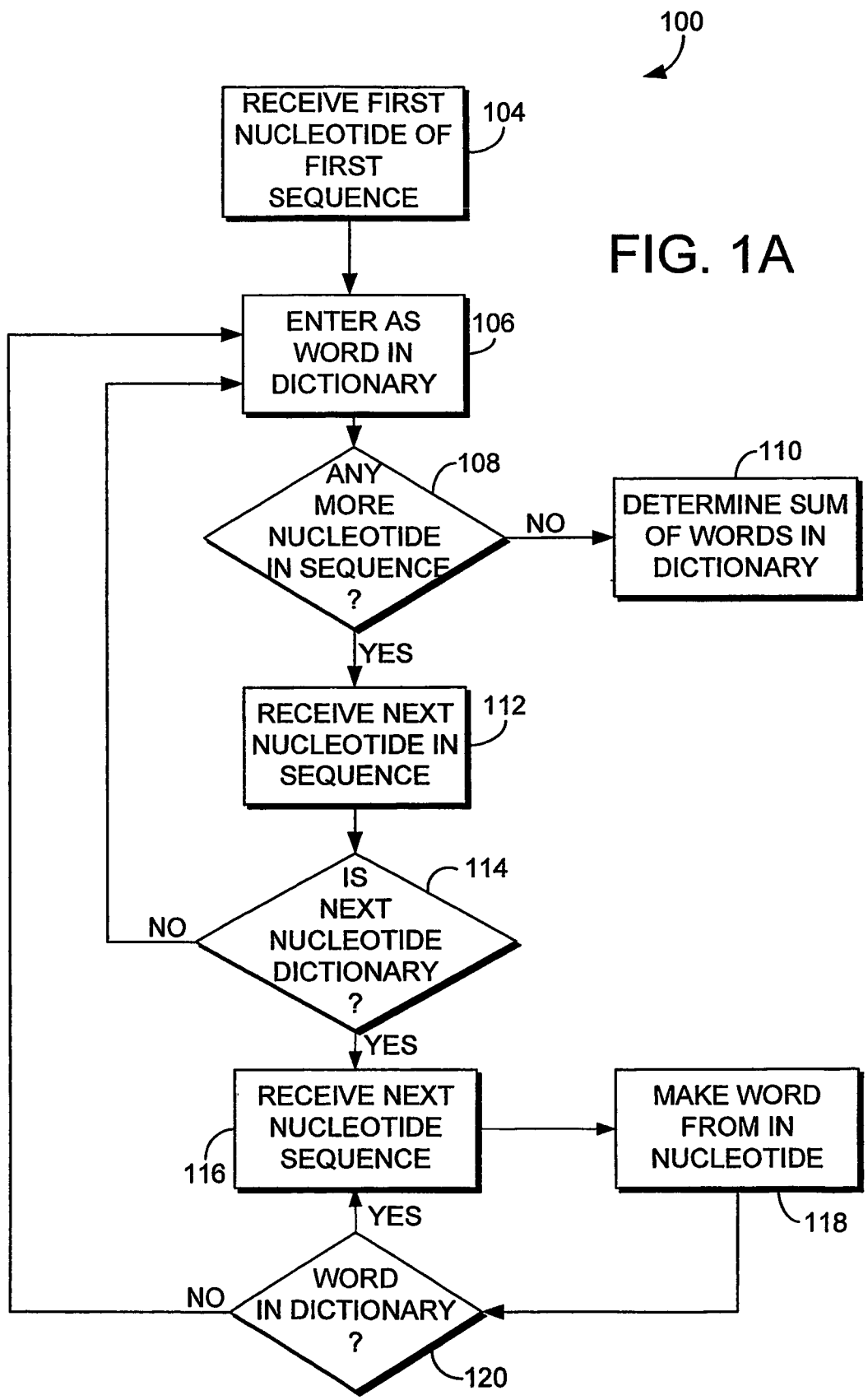
FIG. 1A is a flow diagram of a method for determining the number of sets of nucleotides in a first sequence in accordance with an embodiment of the present invention.

The present invention provides a system and method to ascertain the provenance of a DNA sequence standard approaches use a base-by-base comparison of the unknown sequence with sequences in a database. In the system and method of the present invention a characterization of the target sequence is obtained using algorithms developed, rather than trying to match the DNA sequence of unknown origin and the DNA sequences in a database, base for base. This characterization is compared with characterizations of DNA sequences belonging to different species. As these characterizations are very compact these comparisons can be done very quickly.

Furthermore, as characterizations of DNA sequences belonging to closely related species tend to be more similar than characterizations of DNA sequences belonging to more distantly related species, this allows identification of a DNA fragment at the level of genus even if the DNA sequence of the species is not available. Finally, the characterizations can be obtained with relatively short DNA sequences. Results described below were obtained using sequences from a few hundred bases long to a few million bases long. The system and method of the present invention allows for the identification of the genus and species of origin for a DNA sequence the proposed approach is much more effective.

The characterization of the DNA sequence used is a dictionary of words or database of units that can be used to build that sequence. Given a set of dictionaries corresponding to different genera and an unknown sequence it is possible to identify the sequence as follows: find the distance between the sequence and the dictionaries by counting the number of words in the sequence that are not in a given dictionary. The sequence is then identified with the dictionary closest to it.

The present invention will allow an ab initio approach with the potential for rapid identification of biological materials of unknown origin. An embodiment of the present invention will replace the need for sequencing of DNA for identification of emergent or new organisms without previous phenotypic identification. The technique could also be used in monitoring situations where the need exists for classification of material into broad categories of bacteria, such as Bacillus versus Franciscella, which could have an immediate impact on bio-terrorism prevention.

Let S, Q and R be sequences defined over an alphabet A, $l(S)$ be the length of S, $S(i)$ denote the $i^{th}$ element of S and S $(i, j)$ define the substring of S composed of the elements of S between positions i and j (inclusive). An extension R=SQ of S is reproducible from S (denoted S→R) if there exists an integer $p \le l(S)$ such that $Q(k)=R(p+k-1)$ for $k=1, \ldots, l(Q)$. For example AACGT→AACGTCGTCG (SEQ ID No: 1) with p=3 and AACGT→AACGT AC with p=2.

Another way of looking at this is to say that R can be obtained from S by copying elements from the $p^{th}$ location on in S to the end of S. As each copy extends the length of the new sequence beyond $l(S)$, the number of elements copied can be greater than $l(S)-p+1$. Thus, this is a simple copying procedure of S starting from position p, which can carry over to the added part, Q.

A sequence S is producible from its prefix $S(1,j)$ (denoted $S(1,j) \Rightarrow S$), if $S(1,j) \to S(1,l(S)-1)$. For example AACGT⇒AACGTAC and AACGT⇒AACGTACC both with pointers p=2. Note that production allows for an extra "different" symbol at the end of the copying process which is not permitted in reproduction. Therefore an extension which is reproducible is always producible but the reverse may not always be true.

Any sequence S can be built using a production process where at its $I^{th}$ step $S(1,h_{i-1}) \Rightarrow S(1,h_i)$ (note that $\epsilon = S(1,0) \Rightarrow S(1,1)$). An m-step production process of S results in a parsing of S in which $H(S)=S(1,h_1) \cdot S(h_1+1,h_2), \ldots, S(h_{m-1}+1,h_m)$ is called the history of S and $H_i(S)=S(h_{i-1}+1,h_i)$ is called the $i^{th}$ component of H(S). For example for S=AACGTACC, A·A·C·G·T·A·C·C, A·AC·G·T·A·C·C and A·AC·G·T·ACC are three different (production) histories of S.

If $S(1,h)_i$ is not reproducible from $S(1, h_{i-1})$ [denoted $S(1,h_{i-1}) \to S(1,h_i)$], then $H_i(S)$ is called exhaustive. In other words, for $H_i(S)$ to be exhaustive the $i^{th}$ step in the production process must be a production only, meaning that the copying process cannot be continued and the component should be halted with a single letter innovation. A history is called exhaustive if each of its components (except maybe the last one) is exhaustive. For example the third history given in the preceding paragraph is an exhaustive history of S=AACGT ACC. Moreover, every sequence S has a unique exhaustive history.

Let $c_H(S)$ be the number of components in a history of S. Then the LZ complexity of S is $c(S)=\min\{c_H(S)\}$ over all histories of S. It can be shown that $c(S)=c_E(S)$ where $c_E(S)$ is the number of components in the exhaustive history of S. This is quite intuitive as an exhaustive component is the longest possible at a given step of a production process.

Given two sequences Q and S, consider the sequence SQ, and its exhaustive history. By definition, the number of components needed to build Q when appended to S is $c(SQ)-c(S)$. In a sense, this is the proportional to the number of words in Q that are not present in S. This number will be less than or equal to $c(Q)$ because at any given step of the production process of Q (in building the sequence SQ) uses a larger search space due to the existence of S. Therefore the copying process can only be longer which in turn would reduce the number of exhaustive components. This can also be seen from the subadditivity of the LZ complexity: $c(SQ) \le c(S)+c(Q)$. How much $c(SQ)-c(S)$ is less than $c(Q)$ will depend on the degree of similarity between S and Q.

For example, let S=AACGT ACC ATTG (SEQ ID NO: 2), R=CT AGGG ACTT AT (SEQ ID NO: 3) and Q=ACGGTC ACC AA (SEQ ID NO: 4). The exhaustive histories of these sequences would be:

$$H_E(S) = A \cdot AC \cdot G \cdot T \cdot ACC \cdot AT \cdot TG \quad \text{(SEQ ID NO.2)}$$

$$H_E(R) = C \cdot T \cdot A \cdot G \cdot GGA \cdot CTT \cdot AT \quad \text{(SEQ ID NO.3)}$$

$$H_E(Q) = A \ C \ G \ GT \ CA \ CC \ AA \quad \text{(SEQ ID NO.4)}$$

yielding $c(S)=c(R)=c(Q)=7$. The exhaustive histories of the sequences SQ, and RQ would be:

$$H_E(SQ) = A \ AC \ G \ T \ ACC \ AT \ TG \ ACGG \ TC \ ACCAA \quad \text{(SEQ ID NO:5)}$$

$$HE(RQ) = C \ T \ A \ G \ GGA \ CTT \ AT \ ACG \ GT \ CA \ CC \ AA \quad \text{(SEQ ID NO:6)}$$

Note that it took three steps to build Q in the production process of SQ. On the other hand, five steps were used to generate Q in the production process of RQ. The reason it took more steps in the second case is because Q is "closer" to S than R. In this example this can be observed looking at the patterns ACG and AGG which Q and S share. The number of steps it takes to generate a sequence Q from a sequence S by $c(SQ)-c(S)$ can be formulated. Thus, if S is closer to Q than R then it would be expected that $c(SQ)-c(S)$ is smaller than $c(RQ)-c(R)$ as is the case in the above example. Based on this idea of closeness the four distance measures are defined as:

Distance Measure 1: Given two sequences S and Q, define the function $d(S,Q)$ as.

$$d(S,Q)=\max\{c(SQ)-c(S),c(QS)-c(Q)\}$$

In order to eliminate the effect of the length on the distance measure, a more satisfying function would be the normalized form of $d(.,.)$:

Distance Measure 2: Given two sequences S and Q, define the function $d^*(S,Q)$ as $$d^*(S, Q) = \frac{\max\{c(SQ) - c(S), c(QS) - c(Q)\}}{\max\{c(S), c(Q)\}}$$

Another distance measure that would naturally follow from the idea of building sequence Q using S is the "sum distance". This term is used in the sense that it accounts for the total number of steps it takes to build Q from S and vice versa.

Distance Measure 3: Given two sequences S and Q, define the function $d_1(S, Q)$ as $$d_1(S,Q)=c(SQ)-c(S)+c(QS)-c(Q)$$

Similarly, the normalized version of $d_1(.,.)$ can be defined as follows.

Distance Measure 4: Given two sequences S and Q, define the function $d_1^*(S,Q)$ as *

$$d_1^*(S, Q) = \frac{c(SQ) - c(S) + c(QS) - c(Q)}{c(SQ)}$$

An alternative definition would be $$d_1^{**}(S, Q) = \frac{c(SQ) - c(S) + c(QS) - c(Q)}{\frac{1}{2}[c(SQ) + c(QS)]}$$

A distance metric, $D(\cdot,\cdot)$ should satisfy the following conditions:
1. $D(S,Q) \geq 0$ where the equality is satisfied if $S=Q$ (identity).
2. $D(S,Q)=D(Q,S)$ (symmetry).
3. $D(S,Q) \leq D(S,T)+D(T,Q)$ (triangle inequality).

In order for a metric to be a valid measure of evolutionary change it should also satisfy the following condition:
4. $D(Q,R)+D(S,T) \leq \max\{D(Q,S)+D(R,T),\ D(Q,T)+D(S,R)\}$ (additivity)

With reference to FIG. 1A, a method of determining the number of sets of nucleotides in a first sequence 100 is shown. At step 104 the first nucleotide of a first sequence is received. At block 106, the nucleotide is counted and stored as a word in a dictionary for the first sequence. This process may include storing a nucleotide or set of nucleotides as a unit in a database and/or table. At block 108, it is determined whether there are any nucleotides remaining in the first sequence. If so, at block 112, the next nucleotide in the sequence is received. At step 114, it is determined whether the next nucleotide is a word in the database. If not, the nucleotide is counted and stored as a word in the dictionary or database for the first sequence at step 106.

If the nucleotide is already a word in the dictionary for the first sequence, the next nucleotide of the first sequence is received at step 116. At step 118, the two nucleotides are made into a word or set in the order of being received. In other words, they are a set in of nucleotides in sequential order: the first nucleotide is first letter of the word and the second nucleotide is the second letter of the word. At step 120, it is determined whether the word made from two nucleotides is in the dictionary, database or table of words for the first sequence. If not, the word is counted and stored in the dictionary for the first sequence at step 106. If the word is already in the dictionary of the first sequence then at step 120, the next nucleotide of the first sequence is received. At step 118, a new word is made from the three nucleotides. Steps 116, 118 and 120 are continued until a new word of nucleotides is made that is not in the dictionary of the first sequence.

When at step 120 it is determined that the word created is not in the dictionary of the first sequence it is counted and stored as a word in the dictionary at step 106. This process continues until there are no remaining nucleotides in the first sequence at step 108. Then at step 110 the sum of the words in the dictionary for the first sequence is determined. The sum can later be used for calculating the distances between the first sequence and a second sequence. The method also keeps track of all nucleotides of the first sequence in the order they are received. The first nucleotide sequence can be used with the method described in FIG. 1B.

Figure 1B:
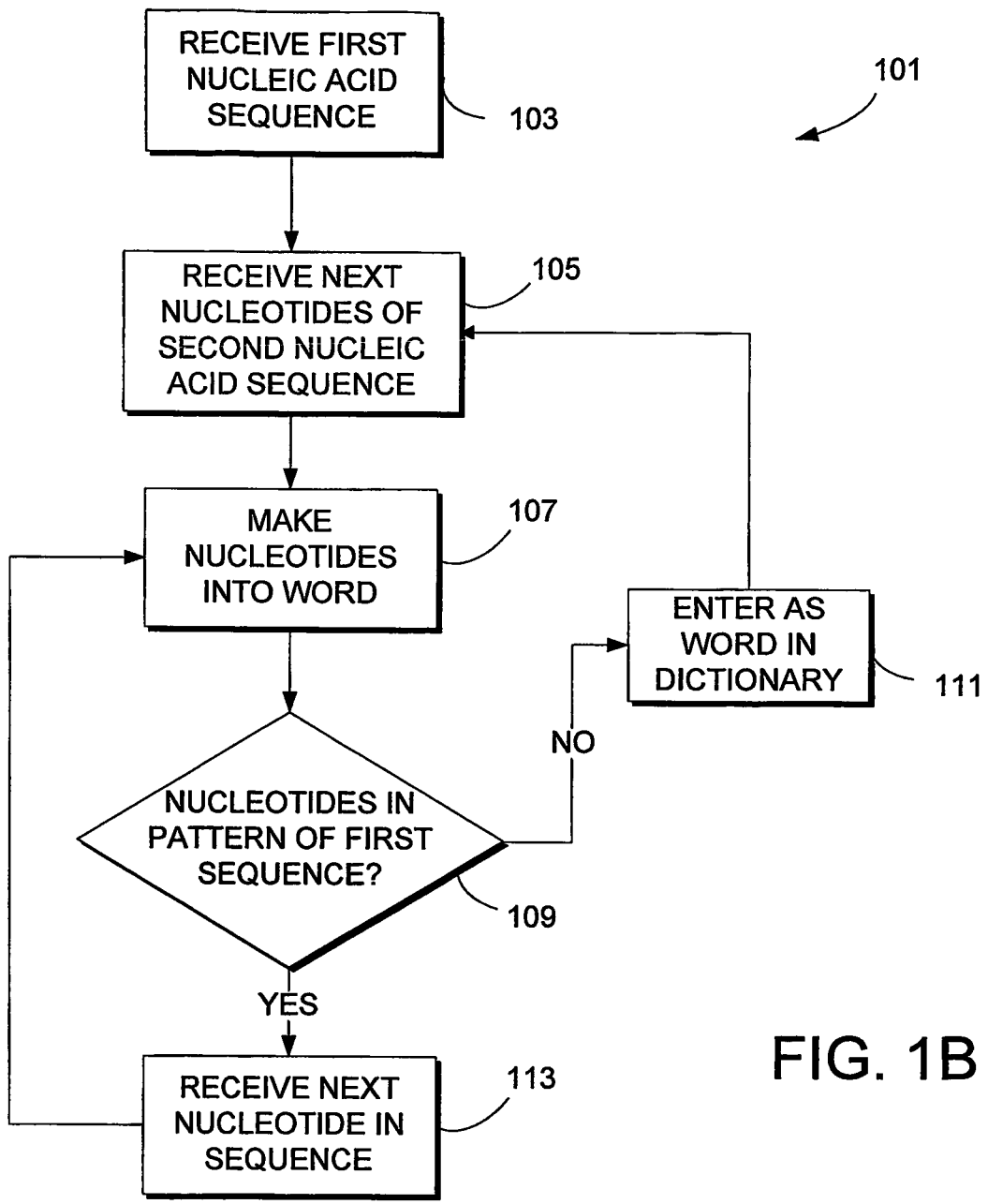
FIG. 1B is a flow diagram of a method for determining the number of sets of nucleotides in a second sequence that are different from the pattern of nucleotides in a first sequence in accordance with an embodiment of the present invention.

With reference to FIG. 1B, a method for determining the number of words of nucleotides in a second sequence that are not in the sequence of nucleotides in a first sequence 101 is shown. At step 103, a first nucleic acid sequence is received. The first nucleic acid sequence can be the one generated by the method described in FIG. 1A or may be received from another table or database. At step 105, the next two nucleotides of the second sequence are received. If this is the beginning of the method, the first two nucleotides of the second sequence are the next two nucleotides received. The nucleotides are made into a word or set at step 107. At this point, the word is two nucleotides long. At step 109, the word is compared to the first sequence to determine if the word is in the nucleotide pattern of the first sequence. If it is not in the first sequence, at step 111, the word is counted and stored as a unit in the dictionary for the second sequence.

If at step 109, it is determined that the word is not in the first sequence, the next nucleotide from the second sequence is received at step 113. At step 107 the nucleotides are made into word or set. In this instance, the word made is three nucleotides long and the nucleotides are in the order received. At step 109, it is determined whether the new word is within the first nucleic acid sequence. Steps 107, 109 and 113 are continued until a new word is made that is not within the pattern of the first nucleic acid sequence. The new word that is not within the pattern of the first nucleic acid sequence is counted and stored as a word in the dictionary for the second nucleic acid sequence at step 111.

The method 101 is continued until there are no more nucleotides in the second nucleic acid sequence. Following, the sum of words in the dictionary for the second sequence is determined. The sum of the words in the dictionary for the first sequence is subtracted from the sum of the words in the dictionary for the second sequence to determine the difference. This difference is used in a number of ways, as described in detail above and in the following examples, to determine the distance of the two sequences from one another.

EXAMPLE 1

In this example it is shown how all four distance measures defined above satisfy the first three conditions and are, therefore, valid distance metrics. The fourth condition was tested by comparing a distance matrix created by the proposed metrics with one reconstructed from the branch lengths of the resulting tree.

LEMMA 1. $c(SQ)-c(S) \leq c(ST)-c(S)+c(TQ)-c(T)$

PROOF. First note:

$$c(STQ)-c(ST) \leq c(TQ)-c(T). \qquad (1)$$

The LHS of (1) is the number of components Q would have when parsed using ST and the RHS is the number of components Q would have when parsed using T. Having ST instead of T cannot increase the number of components in parsing of Q. Since $c(SQ)-c(S) \leq c(STQ)-c(S)$, using (1) we have $c(SQ)-c(S) \leq c(ST)-c(S)+c(TQ)-c(T)$.

COROLLARY 1. $c(Q) \leq c(TQ)$

PROOF. Let $S=\epsilon$, the empty string, in Lemma 1.

Let $S=A^{(n)}$ denote the sequence obtained by n−1 concatenations of the sequence A to itself. For the remainder of this example, if $S=A^{(n)}$, consider S to be equal to A.

THEOREM 1. The function $d(S, Q)$ is a distance metric.

PROOF. By definition $d(\cdot,\cdot)$ satisfies the symmetry condition. The identity condition is satisfied up to an additive error term of $O(1)$ depending on whether the last component of the sequence is exhaustive or not. In order to prove the triangle inequality, show:

$$\max\{c(SQ)-c(S),c(QS)-c(Q)\} \leq \max\{c(ST)-c(S),c(TS)-c(T)\}+\max\{c(TQ)-c(T),c(QT)-c(Q)\}$$

From Lemma 1, here are the following two symmetric inequalities:

$$c(SQ)-c(S) \leq c(ST)-c(S)+c(TQ)-c(T)$$

$$c(QS)-c(Q) \leq c(QT)-c(Q)+c(TS)-c(T)$$

which proves the triangle inequality. Hence, the function $d(S,Q)$ is a distance metric.

THEOREM 2. The function $d^*(S,Q)$ is a distance metric.

PROOF. Again by definition $d^*(\cdot,\cdot)$ satisfies the symmetry condition. The identity condition is satisfied up to an additive error term of $O(1/c(S))$ depending on whether the last component of the sequence S is exhaustive or not. It should be shown that $d^*(\cdot,\cdot)$ satisfies the triangle inequality:

$$\frac{\max\{c(SQ)-c(S), c(S)-c(Q)\}}{\max\{c(S), c(Q)\}} \leq \frac{\max\{c(ST)-c(S), c(TS)-c(T)\}}{\max\{c(S), c(T)\}} + \frac{\max\{c(TQ)-c(T), c(QT)-c(Q)\}}{\max\{c(T), c(Q)\}}$$

Without loss of generality, assume $c(Q) \leq c(S)$.

Case 1: Assume $c(T) \leq c(S)$. In this case:

$$\frac{\max\{c(SQ)-c(S), c(S)-c(Q)\}}{\max\{c(S), c(Q)\}} = \frac{\max\{c(SQ)-c(S)+c(QS)-c(Q)\}}{c(S)}$$

$$\leq \frac{\max\{c(ST)-c(S)+c(TS)-c(T)\}}{c(S)} +$$

$$\frac{\max\{c(TQ)-c(T)+c(QT)-c(Q)\}}{c(S)}$$

$$\leq \frac{\max\{c(ST)-c(S), c(TS)-c(T)\}}{\max\{c(S), c(T)\}} +$$

$$\frac{\max\{c(TQ)-c(T), c(QT)-c(Q)\}}{\max\{c(T), c(Q)\}}$$

where the first inequality follows from Theorem 1 and the second inequality follows from the assumptions.

Case 2. Assume $c(S) \leq c(T)$. Since $c(SQ)=c(Q,S)$ up to a logarithmic factor due to the assumptions we have:

$$\max\{c(SQ)-c(S), c(QS)-c(Q)\}=c(QS)-c(Q)$$

$$\max\{c(ST)-c(S), c(TS)-c(T)\}=c(ST)-c(S)$$

$$\max\{c(TQ)-c(T), c(QT)-c(Q)\}=c(QT)-c(Q)$$

Therefore, the following should be shown:

$$\frac{c(QS)-c(Q)}{c(S)} \leq \frac{c(QT)-c(Q)+c(ST)-c(S)}{c(T)}$$

Since the LHS of the above inequality is $\leq 1$, start by adding the non-negative quantity $c(T)-c(S)$ to both the numerator and denominator of the LHS:

$$\frac{c(QS)-c(Q)}{c(S)} \leq \frac{c(QS)-c(Q)+c(T)-c(S)}{c(T)}$$

$$\log \leq \frac{c(QT)-c(Q)+c(ST)-c(S)}{c(T)}$$

where the last inequality follows from Lemma 1 using it in the form $c(T) \leq c(QT)+c(TS)-c(QS)$ and $$c(T) \leq c(QT)+c(TS)-c(QS) \text{ and } \log_{\leq}$$

means the inequality holds up to a logarithmic factor.

THEOREM 3. The function $d_1(S,Q)$ is a distance metric.

PROOF. By definition $d_1(\cdot,\cdot)$ satisfies the symmetry condition. The identity condition is satisfied up to an additive error term of O(2) depending on whether the last component of the sequence is exhaustive or not. The triangle inequality follows directly from Lemma 1.

THEOREM 4. the function $d_1^*(S,Q)$ is a distance metric (The corresponding theorem and proof for $d_1^{**}$ is almost identical and therefore will not be included here).

PROOF. Again by definition $d_1^*(\cdot,\cdot)$ satisfies the symmetry condition (up to a logarithmic factor). The identity condition is satisfied up to an additive error term of O(2/c(S)) depending on whether the last component of the sequence S is exhaustive or not. Next, prove the triangle inequality for $d_1^*(\cdot,\cdot)$. It suffices to show the two inequalities $$\frac{c(SQ)-c(S)}{c(SQ)} \leq \frac{c(ST)-c(S)}{c(ST)} + \frac{c(TQ)-c(T)}{c(TQ)}$$

$$\frac{c(QS)-c(Q)}{c(SQ)} \leq \frac{c(TS)-c(T)}{c(ST)} + \frac{c(QT)-c(Q)}{c(TQ)}$$

Since these two inequalities are symmetric the first one is provided. Let $\delta = C(TQ)-c(T)+c(ST)-c(S)-[c(SQ)-c(S)]$. From Lemma 1, $0 \leq \delta$. As $[C(SQ)-c(S)]/[c(SQ)] \leq 1$ it follows that $$\frac{c(SQ)-c(S)}{c(SQ)} \leq \frac{c(SQ)-c(S)+\delta}{c(SQ)+\delta}$$

$$= \frac{c(ST)-c(S)+c(TQ)-c(T)}{c(ST)+c(TQ)-c(T)}$$

$$\leq \frac{c(ST)-c(S)}{c(ST)} + \frac{c(TQ)-c(T)}{c(TQ)}$$

since $C(ST)+C(TQ)-C(T) \geq C(ST)$ and $C(ST)+C(TQ)-C(T) \geq C(TQ)$ (from Corollary 1) As the second inequality is proved symmetrically we have $$\frac{c(SQ)-c(S)+c(QS)-c(Q)}{c(SQ)} \leq \frac{c(ST)-c(S)+c(TS)-c(T)}{c(ST)} + \frac{c(TQ)-c(T)+c(QT)-c(Q)}{c(TQ)}$$

which is what needed to be shown.

EXAMPLE 2

In this example it is shown that the proposed distance measures, which are based on the relative complexity between sequences, imply the evolutionary distance between organisms. The distance between sequences S and Q was obtained using the exhaustive histories of the sequences S, Q, SQ and QS. These exhaustive histories were obtained by parsing the sequences using the production rules described earlier. The number of components in he exhaustive histories, $c(S)$, $c(Q)$, $c(SQ)$ and $c(QS)$ were then used as described above to compute the various distance measures.

Phylogenetic analysis based on DNA sequences has been intimately connected with multiple alignment. Hence this embodiment of the present invention can be generally examined based on how well the implicit assumptions used for scoring the multiple alignment agree with particular evolutionary theories. As this embodiment does not depend on multiple alignments the validity of the embodiment is tested in two ways: using simulated data to show that the proposed distance measures can reasonably be represented by a tree. The superiority of the proposed method on existing techniques is shown using this simulated data Secondly, it is determined whether the results generated by the proposed method agree with existing phylogenies. The trees are generated using the neighbor joining (NJ) program [47] in the PHYLIP package. [17] The multiple alignments required by parsimony and maximum likelihood methods are calculated using CLUSTAL W. [56]

Figure 2:
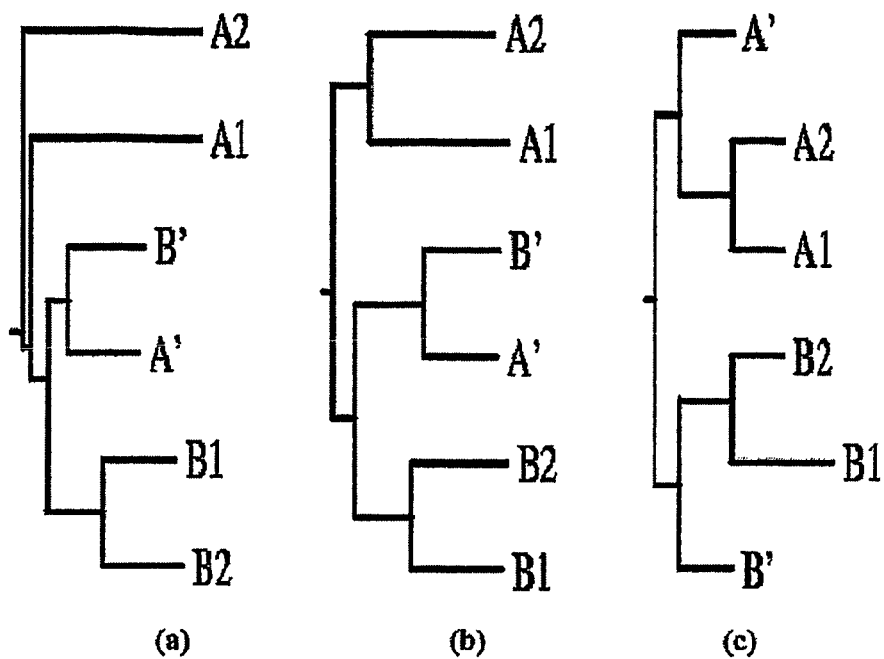
FIG. 2 is a diagram of exemplary phylogenetic trees generated using the method of the present invention compared with phylogenetic trees generated using other methods.

For the simulated data, a 1000 bp sequence was used and evolved into two sequences A" and B" using point mutations (insertions, deletions, substitutions) and segment based modifications (inversions, transpositions, translocations, etc.). Similarly evolved A" evolved into A1 and A2 and B" into B1 and B2. Point mutations were introduced into about 10% of the sequences. Another 10% of the final sequences were a result of sequence rearrangements. These included inversions and translocations. In order to provide length difference and to preserve resemblance to the ancestor sequences, A" into A' and B" into B' were evolved using point mutations only. Sequences A', B', A1, A2, B1 and B2 were used to build phylogenetic trees both using existing methods (maximum likelihood and parsimony) and the proposed method. The results are shown in FIG. 2. In FIG. 2, Phylogenetic trees obtained from the simulated sequences A', B', A1, A2, B1 and B2 using (a) Maximum Likelihood, (b) parsimony and (c) proposed methods are shown.

The trees obtained by all five of the proposed distance measures resulted in identical topologies. In FIG. 2, the consensus tree obtained by those five trees along with the trees obtained by maximum likelihood and parsimony methods is shown. The results show that the true evolutionary topology is achieved by the proposed method only. Both the maximum likelihood and the parsimony trees fail to reflect the relation between A' and A1, A2. In addition, the maximum likelihood tree fails to group A1 and A2 together.

The proposed distance matrix used to build the NJ tree was compared to that reconstructed from the branch lengths of the tree. The purpose was to test additivity of the proposed distance measures. Let M be the distance matrix obtained by the proposed distance measure, T be the tree built using M, and R be the distance matrix reconstructed from the branch lengths of T. In Table 1, below, M, R and |M−R| using d* for the simulated data set are presented. The corresponding results were omitted for the remaining four measures as they are almost identical to the ones presented here. The results in Table 1 show that M and R are very similar to each other, validating the properness of representing the proposed measures with a tree. The maximum percent difference between the corresponding elements of the matrices M and R is 11, with an average percent difference of 2.5.

TABLE 1

Fitness of the NJ tree to the distance matrix

| Seq. | A2 | B1 | B2 | A' | B' |
|---|---|---|---|---|---|
| A1 | 0.7348 | 0.8093 | 0.8104 | 0.7535 | 0.8056 |
| A2 |  | 0.8000 | 0.8046 | 0.7767 | 0.8139 |
| B1 |  |  | 0.7488 | 0.8000 | 0.7674 |
| B2 |  |  |  | 0.8000 | 0.7952 |
| A' |  |  |  |  | 0.7745 |
| A1 | 0.7348 | 0.8015 | 0.8161 | 0.7630 | 0.7180 |
| A2 |  | 0.8056 | 0.8203 | 0.7672 | 0.7221 |
| B1 |  |  | 0.7488 | 0.7878 | 0.7740 |
| B2 |  |  |  | 0.8024 | 0.7886 |
| A' |  |  |  |  | 0.7042 |
| A1 | 0.0000 | 0.0077 | 0.0057 | 0.0095 | 0.0876 |
| A2 |  | 0.0056 | 0.0156 | 0.0095 | 0.0918 |

TABLE 1-continued

Fitness of the NJ tree to the distance matrix

| Seq. | A2 | B1 | B2 | A' | B' |
|---|---|---|---|---|---|
| B1 |  |  | 0.0000 | 0.0121 | 0.0065 |
| B2 |  |  |  | 0.0024 | 0.0065 |
| A' |  |  |  |  | 0.0702 |

Distance matrix used to construct the NJ tree, T; distance matrix reconstructed from the branch lengths of T and the difference of the two matrices are shown respectively.

EXAMPLE 3

In this example, it is shown that the proposed method agrees with existing phylogenies based on both whole genome and individual gene sequences. The phylogeny of eutherian orders has been unresolved due to conflicting results obtained from comparison of Distance matrix used to construct the NJ tree, T; distance matrix reconstructed from the branch lengths of T and the difference of the two matrices are shown respectively whole mtDNA sequences and individual proteins encoded by mtDNA. See [9] Studies using the whole mtDNA sequences suggest the outgroup status of rodents relative to ferungulates and primates [Rodents (Ferungulates, Primates)] while phylogenies using individual proteins confirm the grouping of rodents with primates. There have even been conflicting topologies resulting from the use of different proteins in constructing the evolutionary history.

The first group of sequences was chosen from the controversial data set using the following mtDNA sequences from Gen-Bank; National Center for Biotechnology Information, National Library of Medicine, Building 38A, Bethesda, Md.: human (*Homo sapiens*, V00662), common chimpanzee (*Pan troglodytes*, D38116), pigmy chimpanzee (*Pan paniscus*, D38113), gorilla (Gorilla gorilla, D38114), orangutan (*Pongo pygmaeus*, D38115), gibbon (*Hylobates lar*, X99256), baboon (*Papio hamadryas*, Y18001), horse (*Equus caballus*, X79547), white rhinoceros (*Ceratotherium sinum*, Y07726), harbor seal (*Phoca vitulina*, X63726), gray seal (*Halichoerus grypus*, X72004), cat (*Felis catus*, U20753), fin whale (*Balenoptera physalus*, X61145), blue whale (*Balenoptera musculus*, X72204), cow (*Bos taurus*, V00654), rat (*Rattus norvegicus*, X14848), mouse (*Mus musculus*, V00711), opossum (*Didelphis virginiana*, Z29573), wallaroo (*Macropus robustus*, Y10524) and platypus (*Ornithorhyncus anatinus*, X83427). Rodent species were kept to murids only and marsupials and monotremes were used as outgroup.

Figure 3:
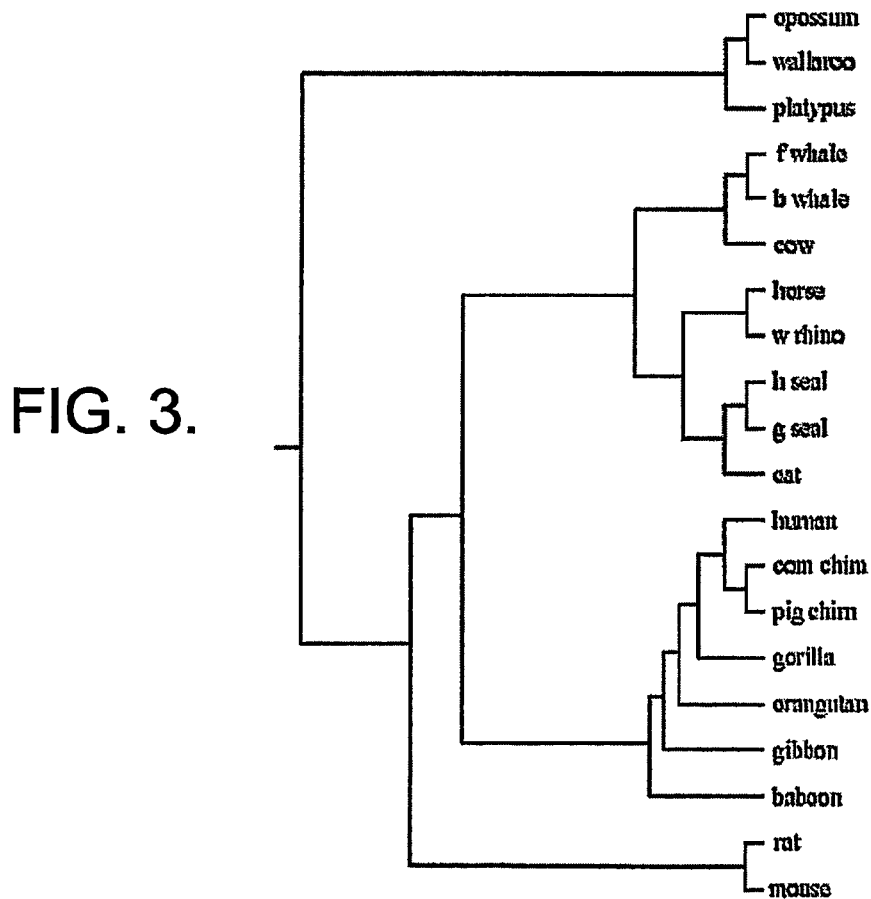
FIG. 3 is an exemplary phylogenetic tree generated using other methods.

The proposed distance measures to the complete mitochondrial genomes listed above were applied. All five metrics (d, d*, $d_1$, $d_1$* and $d_1$**) resulted in identical trees. In FIG. 3, the consensus of these five trees is shown. The tree is in complete agreement with Cao et al. (1998) [9] confirming the outgroup status of rodents relative to ferungulates and primates. In FIG. 3, the topology for eutherians using whole mtDNA where wallaroo, opossum and platypus were used as outgroup. The second data set is an extension of the first one obtained by the addition of non-murid rodents (squirrel, dormouse and guinea pig) and more ferungulate sequences. The Gen-Bank accession codes for these additional mtDNA sequences are as follows: squirrel (*Sciurus vulgaris*, AJ238588), fat dormouse (*Glis glis*, AJ001562), guinea pig (*Cavia porcellus*, AJ222767), donkey (*Equus asinus*, X97337), Indian rhinoceros (*Rhinoceros unicornis*, X97336), dog (*Canis familiaris*, U96639), sheep (*Ovis aries*, AF010406), pig (*Sus scrofa*, AJ002189), and hippopotamus (*Hippopotamus amphibius*, AJ010957). This more controversial data set deals with the relative positions of two rodent clades, murids and non-murids (whether there is rodent monophyly, paraphyly or polyphyly) and the phylogenetic position of guinea pigs. [10] [43]

Figures 4, 5:
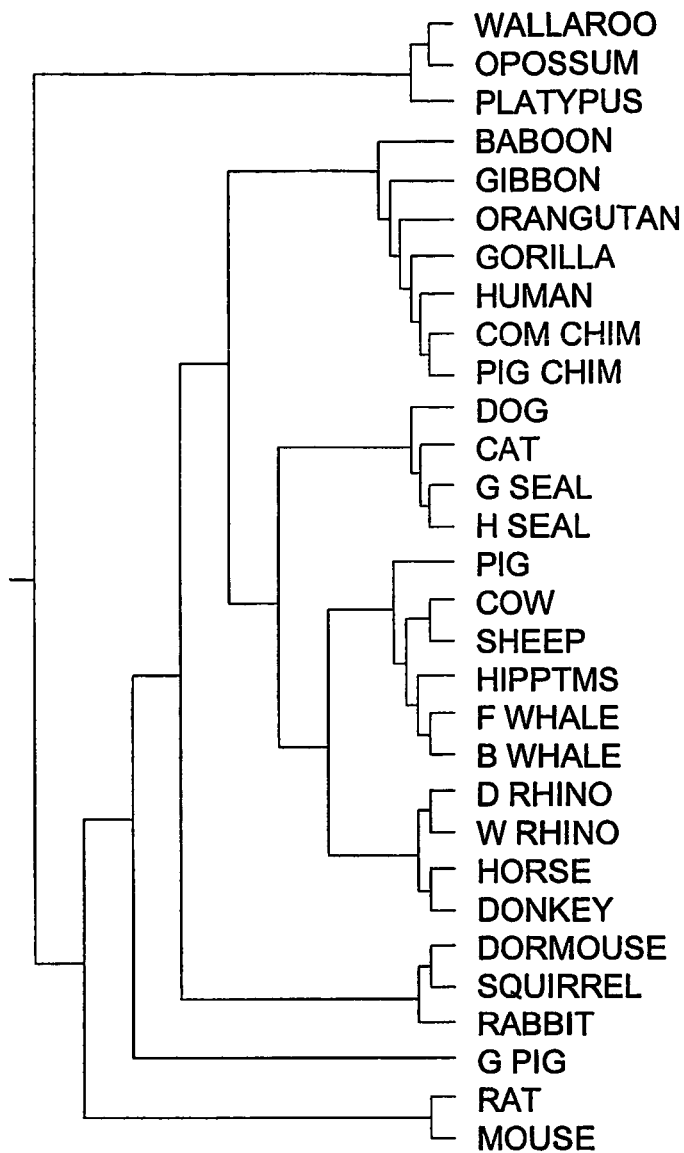
FIG. 4 is an exemplary phylogenetic tree generated using the method of the present invention.
FIG. 5 is an exemplary table generated using the method of the present invention.

The resulting trees from the five distance metrics were in agreement for the most part. All of the metrics confirmed rodent paraphyly (except for d which suggested rodent monophyly) and guinea pig was not grouped with either rodent clade in each case (except for d* which suggested grouping of guinea pig with nonmurids). The consensus tree of the five trees obtained using the proposed metrics is shown in FIG. 4. In FIG. 4, the consensus tree for the proposed distance metrics using complete mtDNA. The consensus phylogeny is in agreement with Reyes et al. (2000) [43] except for the position of guinea pig which remains an open question. [10] FIG. 4 groups squirrel with dormouse, which has shown to be based on strong molecular, palaeontological and morphological evidence. See [43] On the other hand, nonmurid rodents are placed at the base of primates and ferungulates with murids being an early branch of the tree (suggesting rodent paraphyly), which is presented as the most likely hypotheses by Reyes et al. (2000) [43].

The results presented in FIGS. 3 and 4 are in accord with (Li et al., 2001) [36], which also applied an information theoretic distance measure to these data sets. However, mammalian phylogeny still remains to be a controversial topic. Two recent studies suggest a monophyletic clade of rodents and primates. [40] [42] As noted earlier, conflicting results have been reported regarding the phylogeny of eutherian orders based on whole genome sequences or individual genes. The sequences used in Madsen et al. (2001) [40] and Murphy et al. (2001) [42] use individual genes to build the trees. The data sets used in these two studies differ from each other and the data sets used in this paper, which could result in varying topologies.

Both of these analyses used the whole mitochondrial genomes of the species. The results are not based on the phylogenies inferred using coding regions or individual proteins. Instead the complete sequences as opposed to partial genome data were used. The phylogenies inferred using the proposed distances confirm that our method can successfully construct evolutionary histories using whole genome sequences.

EXAMPLE 4

The LZ-complexity of a sequence was obtained by counting the number of steps needed to generate a copy of the primary sequence starting from a null state. Each step involved a process of copying a nucleotide or a series of nucleotides for a sequence and then adding the next nucleotide from the sequence being analyzed. The number of steps needed to obtain the exhaustive library was identified as the LZ-complexity value of the given sequence. For example, the LZ-complexity of the simple sequence 'ATGTGAATG' would be obtained as shown in FIG. 5. Since five steps were needed to generate the exhaustive library, the LZ-complexity value of the analyzed sequence was '5'. If long fragments of repeat sequence had been present, the number of steps required to construct the exhaustive library would have been small compared to a random nonrepetitive sequence. A random nonrepetitive sequence generates a high LZ-complexity value. The complexity of a sequence 'X' compared to a sequence 'Y' is known as the RCM of 'X' with respect to 'Y'. This is the number of steps required to construct sequence 'X' beginning with the set of nucleotide sequences used to construct 'Y'. The RCM of sequence 'X' with respect to 'Y' is defined as the number of production steps required to construct an exhaustive library of nucleotide combinations of sequence 'X' beginning with the exhaustive library of nucleotide combinations within sequence 'Y'. The exhaustive library of a sequence is defined as the smallest number of distinct nucleotides or nucleotide combinations required to construct the sequence using a copying process. Mathematically, the distance 'D' between two sequences 'X' and 'Y', is defined as: $D(X, Y) = \max\{RCM(X, Y), RCM(Y, X)\}/\max\{RCM(X, \_), RCM(\_, X)\}$, where _ represents the empty sequence. The distance matrix is a two dimensional table where the element in the 'Ith' row and the 'Jth' column are the distances between the 'Ith' and 'Jth' sequence.

The method may also be described with reference to FIG. 5 where steps involved in generating an exhaustive library of a given sequence ATGTGAATG are shown. In step 1, the first nucleotide from the analyzed sequence is added to generate a new sequence 'Z'. In step 2, the analyzed sequence is scanned and any new nucleotides not present in the generated sequence are added, ('T' is added to the sequence 'Z' generated in Step 1 to give A,T). In step 3, the analyzed sequence is scanned for the presence of new nucleotide combinations. Finding none in the example, the nucleotide 'G' is added to 'Z' to generate A,T,G. In step 4, the next nucleotide in the analyzed sequence is scanned to copy TG from the most recently generated sequence 'Z' and 'A' added to generate the sequence A,T,G, TGA. In step 5, ATG is copied from the newly generated sequence 'Z' to give the final sequence of A,T,G,TGA,ATG. The A,T,G,TGA,ATG constitute the exhaustive library of nucleotides for the analyzed sequence ATGTGAATG, resulting in the LZ-complexity value to equal 5 based on the number of steps required.

Identical taxon samples for the cytochrome b gene ranging in size from 396 to 1158 bp were used from published source. [58] The 18S rDNA sequences ranging from 1683 to 1800 bp was identical to the published source. [26] The 467 to 709 bp ITS sequences (which included the 5.8S genomic region) used in this study were obtained using the methods of Henry et al. (2000) [64] and included the following (Accession numbers from GenBank, National Center for Biotechnology Information, National Library of Medicine, Building 38A, Bethesda, Md. 20894): *Ajellomyces capsulatus* (AB071828 to 31 and AF038353), *Ajellomyces dermatitidis* (AF183912 and AF038358), *Arthroderma benhamiae* (AF038359), *Aspergillus flavus* (AF138287), *A. fumigatus* (AF13828), *A. niger* (AF138904), *A.* sp. (AJ001332), *A. terreus* (AF138290), *A. ustus* (AF157507), *Auxarthron umbrinum* (AY177308), *A. umbrinum* (AY177309), *Byssochlamys fulva* (AY306014), *Cladophialophora bantiana* (AF131079), *Cordyceps capitala* (U57668), *Emericella nidulans* (AF138289), *Eupenicillium pinetorum* (AY354240), *Eurotium repens* (AY360405), *Filobasidiella neoformans* (AF162916), *Fusarium oxysporum* (AF165875), *Geosmithia argillacea* (AF033389), *G. cylindrospora* (AF033386), *G. emersonii* (AF033387), *G. lavendula* (AF033385), *Gymnascella hyalinospora* (AF129853 and AF129854), *Hamigera avellanea* (AB105350), *H. striata* (AF454074), *H. striata* (AF454073), *Hypoxylon cohaerens* (AJ390399), *Malbranchea dendritica* (AY177310), *Monascus purpureus* (AF458473), *Monascus* sp. (AF458474-76), *Haematonectria haematococca* (AF165874), *Paracoccidioides brasiliensis* (AF038360), *Pseudallescheria boydii* (AF181558), and *Trichophyton tonsurans* (AB094675, AB094674, AB094659, AB094658). The *Coccidioides inmitis* sequence was obtained.

Generation of distance matrix and phylogenetic tree construction The relative complexity measure (RCM) for creation of the distance matrix was utilized as previously described. The distance-based trees were generated with the neighbor-joining option of the phylogeny inference package, PHYLIP 3.5c using the RCM algorithm generated distance matrix as input. [17]

For the set of fungal sequences, distances between all pairs were calculated and used to construct a distance matrix. The RCM was used to determine the distance matrices from each of the three molecular targets (cytochrome b gene, 18S rDNA gene and the combined ITS regions). These distance matrices were used by the neighbor-joining algorithm to obtain the respective phylogenetic trees. To determine the discriminatory power of RCM, phylogenetic trees were compared with previously published trees for cytochrome b and 18S rDNA sequences. For the analysis of cytochrome b sequences, the distance between the sequences was calculated using Kimura's two-parameter model. [58] A total of 26 datasets were included in the analysis. The cytochrome b sequences were analyzed using 1000 bootstrap-resampled data sets by neighbor-joining method to access the branch point support values. [58] However, the phylogenetic analysis of aligned 18S rDNA sequences of 35 *Onygenales*, four *Eurotiales* species, and one *Chlaetothyriales* (as outgroups) were done using a maximum-likelihood multiple-hit correction with an empirical transition/transversion ratio, empirical base frequencies, a gamma distribution of 0.5, and four categories of variations. [26] The support values for the branches were obtained from 1000 bootstrap-resampled data sets used for analysis by both the neighbor-joining and parsimony methods. [26]

The robustness of the proposed RCM approach was tested by examining the impact on the topology of the phylogenetic tree by reducing the overall length of the cytochrome b gene, ITS regions, and 18S rDNA gene sequences. Seven medically relevant fungal sequences were chosen and phylogenetic trees were generated by progressive removal of 10, 20, 30, 40 and 50% of the three original target sequences from either the 5' or the 3' ends. A comparison of the topology of phylogenetic trees obtained with the reference method and the RCM approach was done.

Figure 6:
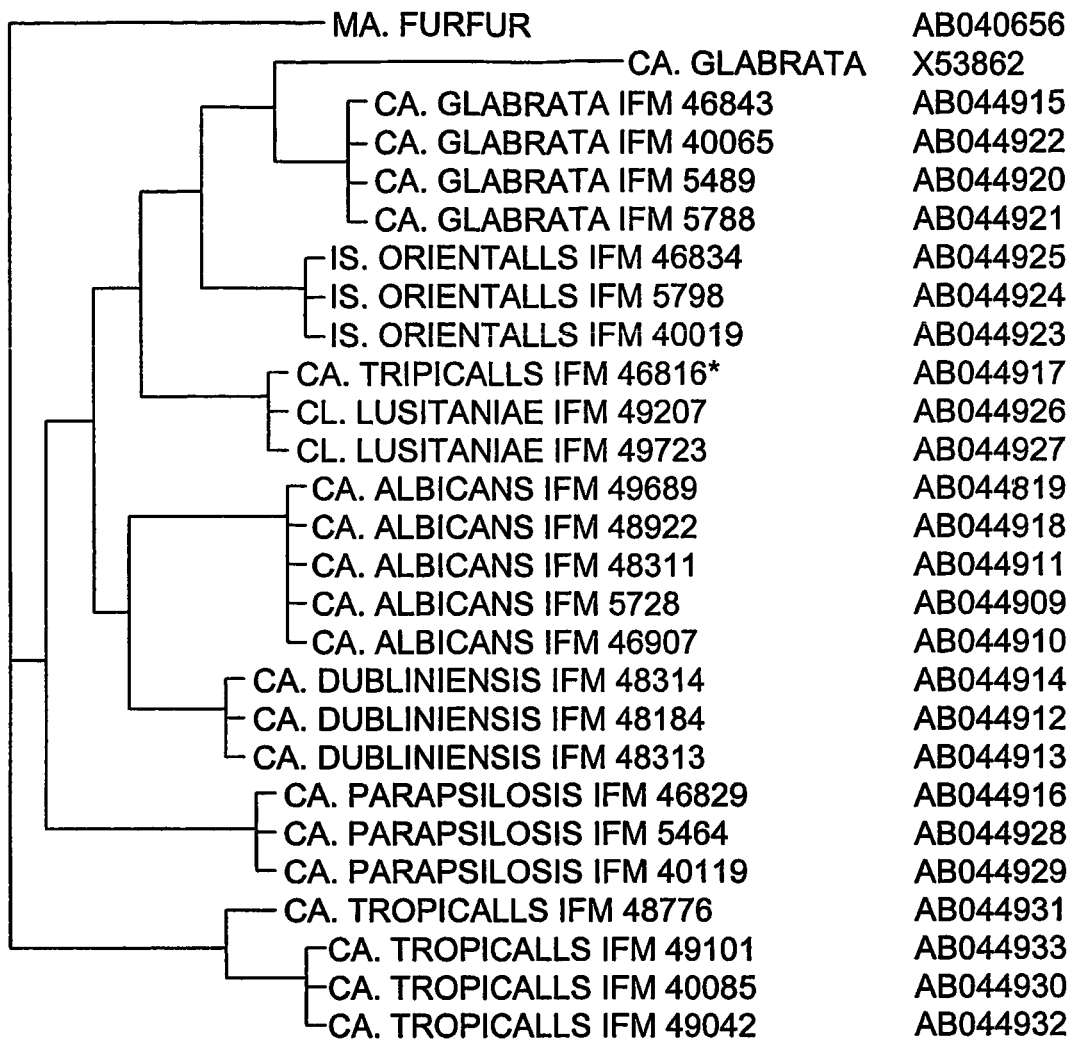
FIG. 6 is an exemplary phylogenetic tree generated using the method of the present invention.

The cytochrome b gene sequences from multiple isolates of the order *Saccharomycetales* together with the sequence for *Malassezla furfur* as an outgroup, were evaluated to test the discriminatory power of the relative complexity measure (RCM) approach (FIG. 6). Referring to FIG. 6, a neighbor-joining tree of the most common *Candida* species based on nonaligned nucleotide sequences for the cytochrome b gene using the RCM approach is shown. Items designated with (*) refer to nucleotide sequence showing 100% identity to *C. lusilaniae* cytochrome b sequence. *Malassezia furfur* sequence was used as an outgroup for the analysis. Cl.=*Clavispora*, Ca.=*Candida*, Is.=*Issatchenkin*, Ma.=*Malassezia*. The GenBank accession numbers are included for each species/strain. Consistent with the previously published phylogenetic relatedness of *Candida* sp. using aligned sequences for construction of a tree, RCM showed similar topology for the multiple strains of this species. However, *Candida tropicalis* (AB044917) grouped together with *Clavispora lusitanieae* and subsequent analysis showed that both have 100% sequence identity. The RCM approach was applied to identical taxon samples of previously published 18S rDNA sequences, a commonly used and widely accepted target gene for phylogenetic analysis.

Figure 7:
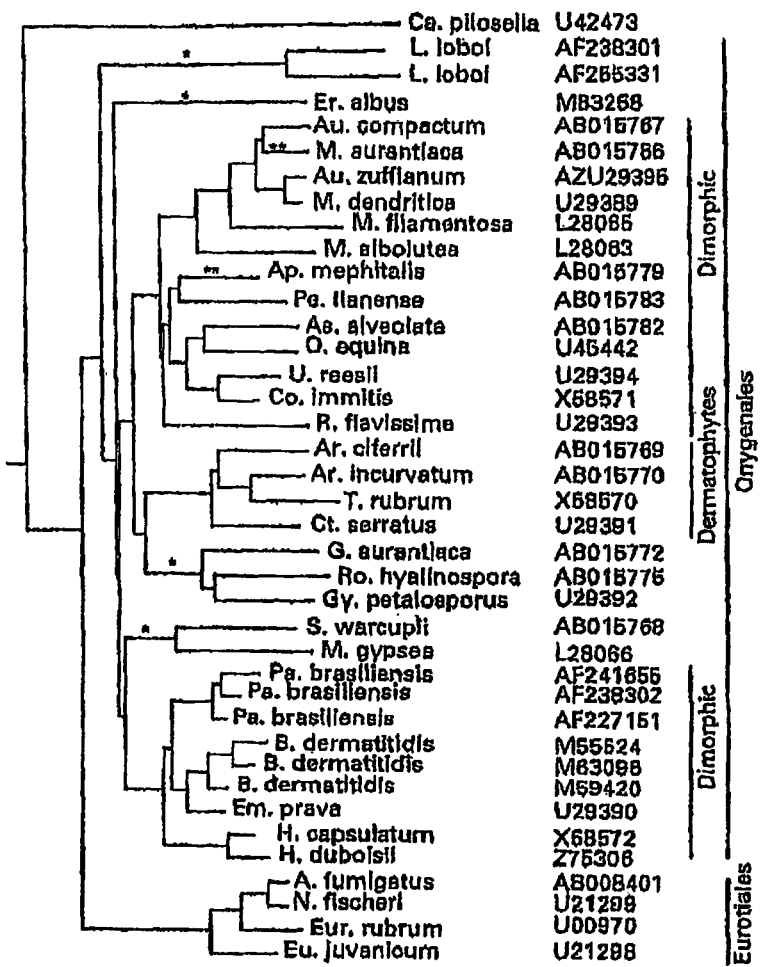
FIG. 7 is an exemplary phylogenetic tree generated using the method of the present invention.

A comparison between the trees generated by non-aligned sequences using the RCM approach to the previously published trees that used aligned sequences demonstrated an overall similar topology except for the addition of a branch containing *Eremascus albus* (FIG. 7). Referring to FIG. 7, neighbor-joining tree of nonaligned 18S rDNA sequence of *Onygenales*, *Eurotiales* and *Chaetothyriales* generated using the RCM approach. The differences in the relatedness that is observed compared to the previously published tree that used maximum-likelihood multiple-hit correction methods on aligned sequences are marked (*, branch; **, within the lade) and summarized in results. The orders and morphological groupings are shown on the right with vertical bars. A.=*Aspergillus*, Ap.=*Aplianoascus*, Ar.=*Arthroderma*, As.=*Ascocalvatia*, B.=*Blastomyces*, Co.=*Coccidioides*, Ct.=*Ctenomyces*, Eur.=*Eurotium*, Em.=*Emmonsia*, Er.=*Eremascus*, Eu.=*Eupencillium*, G.=*Gymnascella*, Gy.=*Gymnoascoideus*, H.=*Histoplasma*, L.=*Lacazia*, M.=*Malbranchea*, N.=*Neosartorya*, O.=*Onygena*, P.=*Pectinotrichum*, Pa.=*Paracoccidiodes*, R.=*Renispora*, Ro.=*Rollandina*, S.=*Spiromastix*, T.=*Trochophyton*, U.=*Uncinocarpus*. GenBank accession numbers are indicated for each species/strain.

The *Eurotiales* (*Aspergillus fumigatus*, *Neo-sartorya fischeri*, *Eurotium rubrum* and *Eupenicillium javanicum*) and the *Onygenales* formed two lade consistent with previous studies. However, some variable topology was apparent among some species of *Onygenales* formed two clade consistent with previous studies. However, some variable topology was apparent among some species of *Onygenales*.

The RCM approach separated *Lacuzia loboi* distant to the remaining dimorphic fungi which include *Paracoccidiodes brasiliensis*, *Blastomyces dermatitidis*, *Emmonsia parva*, and *Histoplasma capsulatum*. The lade containing the saprophytic *Spiromastix warcupii* and the keratinophilic fungus *Malbranchea gypsea* showed a close relatedness to the dimorphic fungi. In contrast to the phylogenetic tree depicting the relatedness of *Eremascus albus* to the dermatophytes including *Ctenomyces serratus*, *Arthroderma incurvatum*, *Trichophyton rubrum* and *Arthroderma ciferrii*, the RCM resulted in a distinct phylogenetic position for *E. albus*. Further, this close relatedness with the dermatophytes was replaced by a clad containing the members of *Gymnoascocene* (*Gymnascella auruntiaca*, *Rollandina hyalinospora* and *Gymnoascoideus petalosporus*).

Figure 8:
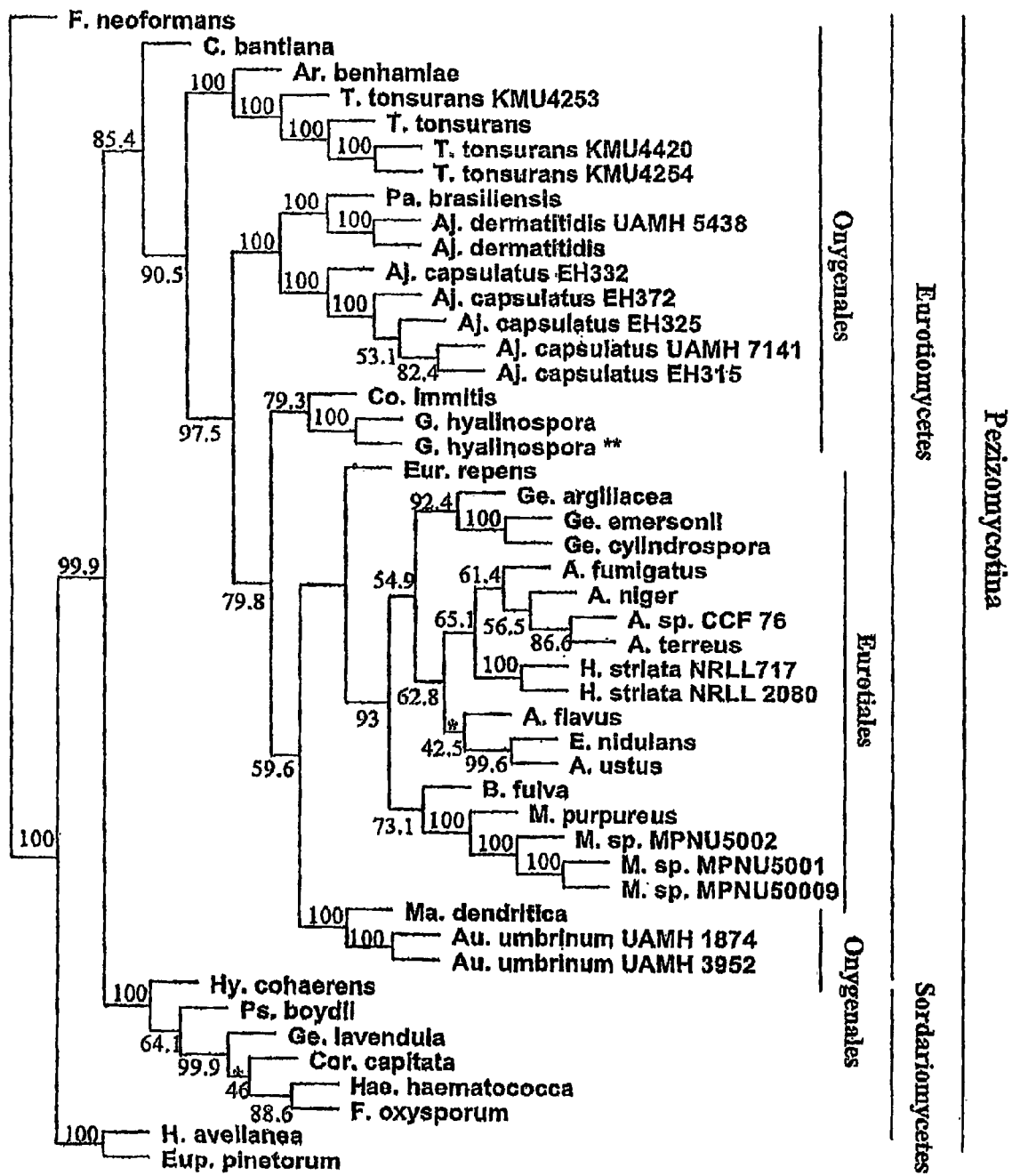
FIG. 8 is an exemplary phylogenetic tree generated using the Jukes-Cantor method.

The RCM approach was also applied to ITS sequences from 47 taxons of the subphylum *Pezizomycotina* (*Euascomycotina*) including 39 *Eurotiomycetes* (20 *Eurotiales*, 19 *Onygenales*), 6 *Sordariomycetes*, 1 *Chaetothyriomycetes*, and a member of *Basidiomycota* as the outgroup. These included 17 medically important fungi, representing three different fungal orders. Comparison of the trees using the RCM approach with the trees constructed with identical taxon samples using standard methods requiring sequence alignment demonstrate an overall similar topology with some variation in outer branching. The distance based tree generated with the unweighted pair group method with arithmetic mean (UPGMA) option of the PHYLIP 3.5c using the Jukes-Cantor algorithm gave the best boot strap values for branching (FIG. 8) throughout the tree compared to the trees generated with neighbor-joining option or the use of other distance matrix algorithm.

Figure 9:
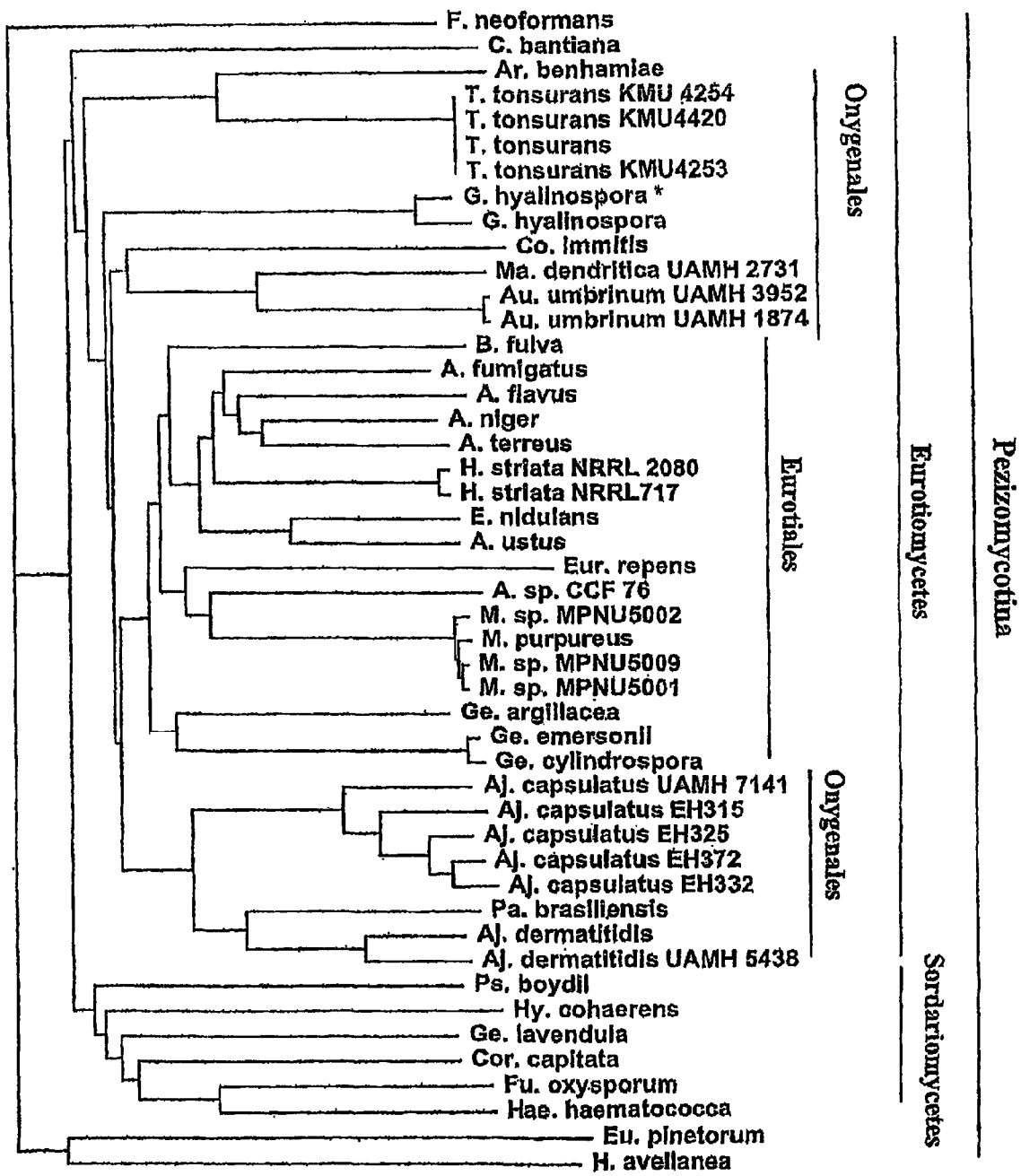
FIG. 9 is an exemplary phylogenetic tree generated using the method of the present invention.

Referring to FIG. 9, phylogenetic relationship of 17 medically relevant fungi among 47 genera of *Pezizomycotina* based on rDNA ITS1-5.8S gene-ITS2 sequence is shown. Distance based trees were generated with the (a) UPGMA using Jukes-Cantor algorithm and the (b) Neighbor-joining method using RCM algorithm. The significance of the branches in the UPGMA tree was tested by bootstrap analysis using 1000 bootstrap replications. Branches showing bootstrap values less than 50% are designated by *. Sequences were obtained from clinical isolates are: A.=*Aspergillus*, Aj.=*Ajellomyces*, Au.=*Auxarthron*, B.=*Byssochlamys*, C.=*Cladophialophora*, Co.=*Coccidlioides*, Cor.=*Cordyceps*, E.=*Emericella*, Eur.=*Eurotium*, Eu.=*Eupenicillium*, F.=*Filobasidiella*, Fu.=*Fusarium*, G.=*Gymnascella*, Ge.=*Geosinithia*, H.=*Hamlgera*, Hae.=*Haematonectria*, Hy.=*Hypoxylon*, M.=*Monascus*, Ma.=*Malbranchea*, Pa.=*Paracoccidioides*, Ps.=*Pseudallescheria*, T.=*Trichophyton*. Strain numbers are included where available. GenBank accession numbers for these genera are listed in the Material and Methods section.

The topology presented by this tree compared well with the tree generated with neighbor-joining option using the distance matrix generated by using RCM algorithm, except for the positioning of *Coccidioides immitis, Eurotium repens, Aspergillus* sp. CCF76 and *Byssochlamys fulva* (FIG. 9). However, a close relationship among molds and the dimorphic fungi was evident (FIG. 9). With an exception of *Eupenicillium pinetorium* and *Hamigera avellanea*, the RCM approach separated *Eurotiales, Onygenales* and the members *Sordariomycetes* into distinct clusters (FIG. 9). The *Arthroderma benhamiae*, a teleomorph of *Trichophyton* grouped together with *Trichophyton tonsurans*. Similarly, *Malbranchea dendritica*, a teleomorph of *Auxarthron* grouped together with *Auxarthron umbrinum*.

Figure 10:
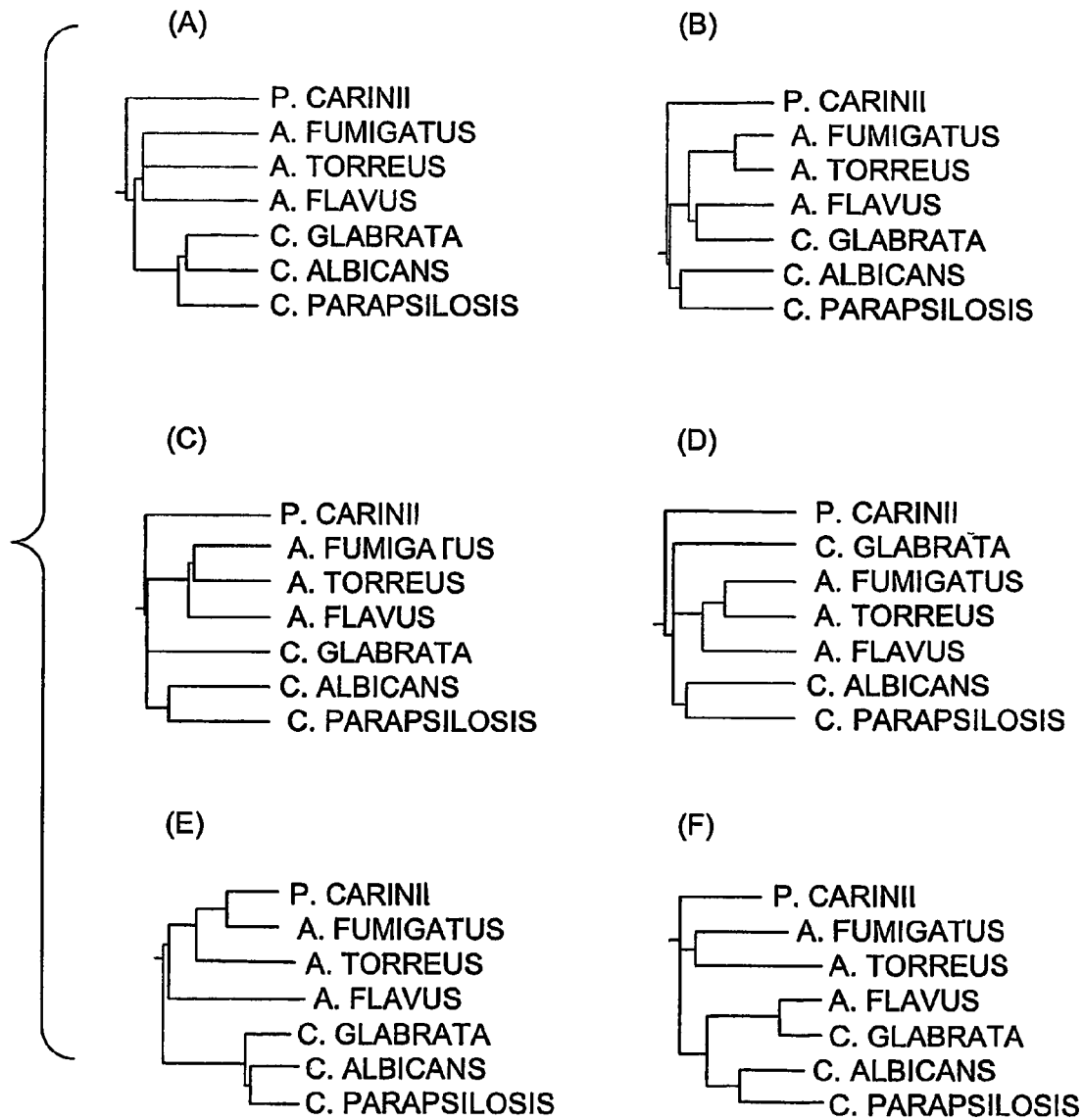
FIG. 10 includes exemplary phylogenetic trees using the method of the present invention where portions of the genetic sequence have been deleted.

The reliability and robustness of the RCM approach was tested by examining the impact upon topology integrity by progressively deleting portions of the target genes. The phylogenetic trees generated after removal of 10, 20, 30, 40 and 50% of the three original target sequences from seven fungal species showed target sequence-dependent difference in the level of robustness (FIG. 10). Neighbor-joining trees of non-aligned cytochrome b gene (A, B), ITS1-5.8S-ITS2 region (C, D) and 18S gene (E, F) sequences generated using the RCM approach are shown. The trees on the left of FIG. 10 used full-length sequences and the trees on the right used randomly deleted partial sequences for analysis (deletion of 50% of cytochrome b gene sequences, 40% of ITS1-5.8S-ITS2 region sequence and 30% of the 18S target gene sequence). Vertical lines indicate change in topology.

The RCM generated trees retained appropriate topology after removal of up to 50% of the cytochrome b gene sequence, 40% of the ITS sequence, and 30% of the 18S rDNA gene target sequence. In comparison, both reference methods failed to maintain baseline topology after removal of only 10% of the sequence. Deletion from either the 5' or 3' end had no impact on the outcome.

The relative complexity measure (RCM) evaluates the relatedness of DNA sequences with an advantage to not require alignment of sequences prior to analysis. Three genetic targets from fungi, including the mitochondrial cytochrome b gene, the 18S rDNA gene, and the ITS-1 and ITS-2 regions of the rDNA gene complex, were evaluated using the RCM approach to depict species relatedness.

Using the cytochrome b gene sequence, the RCM approach separated closely related *Candida* species. Consistent with an earlier report, strains of *C. tropicalis, C. albicans* and *C. glabrata* showed intraspecies variation. RCM successfully detected the reported two DNA types due to 1.8% sequence variation for *C. tropicalis*. In addition, a 0.3% sequence variation reported for *C. albicans* and *C. glabrata* were apparent (FIG. 6). *Candida dubliniensis* showed a distinct phylogenetic position in relation to *Candida albicans*. The topologies obtained with the RCM approach closely resembled UPGMA trees described by Yokoyama et al. (2000) [58]. These observations reflect the sensitivity and comparability of RCM approach with the standard algorithmic approaches.

The RCM approach when applied to 18S rDNA sequences from 33 different fungal species (28 *Onygenales*, 4 *Eurotiales*, and 1 *Chaetothyriales*) generated similar topology to that obtained from the method using multiple aligned sequences. [26] Based on fruiting body structures, the phylogenetic positioning of *Eremascus albus* had been problematic due to a lack of diagnostic cleistothecial morphology. *Ereinascus albus* has been alternatively classified with yeast or in the class Plectomycetes, which includes genera producing cleistothecia. [5] The RCM approach showed a distinct phylogenetic position for *Eremascus albus*. The phylogenetic positioning of *Capronia pilosella* and the species in the *Eurotiales* strengthened the discriminating power of the RCM approach. The *Capronia pilosella* sequence was used as an outgroup sequence in the standard approach [26] and was appropriately outgrouped without the need for multiple sequence alignment. Consistent with earlier observations, species within the *Eurotiales* were grouped appropriately into one clade (FIG. 7). In contrast to the close phylogenetic affinities observed between *Paracoccidiodes brasiliensis* and *L. loboi* [26] the RCM approach separated *l. loboi* distant from the remaining dimorphic pathogens. The observed differences may be due to inaccuracies in the DNA sequence as submitted to GenBank. [58]

Recent studies have demonstrated the discriminatory power of the ITS regions to identify medically important yeasts. The RCM approach when applied to the ITS regions of the rDNA gene complex generated similar topology to that obtained from the method using multiple aligned sequences that showed strong bootstrap values for the branching. Differences in the outer branching could be attributed to the varying positions of *Byssochlamys fulva, Aspergillus* sp. CCF76 and *Eurotium repens*. Consistent with earlier reports, the branching order suggests that the anamorphic genus *Geosmithia* is a polyphyletic taxon. The dimorphic fungal pathogens including *P. brasillensis* clustered together with in the *Onygenales* as defined by a basal branch supported by 100% of the UPGMA bootstrapped data sets. Other members of the *Onygenales* including *Coccidioides immitis* show some variation in the evolutionary origins and the bootstrap values for these branches are relatively weaker. It is interesting to note that *H. avellanea* and *E. pinctorum* are outgrouped by both methods of analysis suggesting a possible misidentification of these sequences.

The robustness and reliability of the RCM approach was demonstrated by trees generated with appropriate topology after removal of up to 50% of the cytochrome b gene, 40% of the ITS sequences and 30% of the 18S gene target sequence.

The examples above demonstrate the multiple advantages of the RCM approach over standard phylogenetic tree construction approaches. These advantages included the elimination of a requirement for sequence alignment to obtain a distance matrix, the ability to analyze short diverse sequences, the lack of need for operator involvement in choosing the aligned sequence, and the avoidance of reliance on a predetermined, arbitrary decision tree. These advantages are expected to contribute towards whole genome phylogeny.

The present invention relates to a new sequence distance measure and its variations. The proposed metric uses LZ complexity which relates the number of steps in a production process of a sequence to its complexity. A sequence from a different sequence is generated linking the resulting number of steps to the 'closeness' between two sequences. Unlike most existing phylogeny construction methods, the proposed method does not require multiple alignment and is fully automatic. Therefore, comparisons can be performed at the whole genome level where multiple alignment based strategies fail. Unequal sequence length or the relatively different positioning of similar regions between sequences (such as different gene order in genomes) are not problematic as the proposed method handles both cases naturally. Moreover, no approximations and assumptions were used in calculating the distance between sequences. The method utilizes the entire information contained in the sequences and require no human intervention. The results show that the proposed method can successfully construct phylogenies using either whole genomes or single genes. This will be useful as genome level phylogeny construction becomes important with the arrival of such data.

Although the invention has been described with reference to embodiments of the invention and the attached drawing figures, it is noted that substitutions may be made and equivalents employed herein without departing from the scope of the invention as recited in the claims. For example, additions steps may be added and other steps omitted without departing from the scope of the invention.

REFERENCES

[1] Apostolico, A. and Lonardi, S. (2000) Compression of biological sequences by greedy off-line textual substitution. In Storer, J. A. and Cohn, M. (eds.), *IEEE Data Compression Conference, DCC*, IEEE Computer Society TCC, Snowbird, Utah, pp. 143-152.
[2] Barry, D. and Hartigan, J. A. (1987) Statistical analysis of hominoid molecular evolution. *Stat. Sci.*, 2, 191-210.
[3] Benedetto, D., Caglioti, E. and Loreto, V (2002) Language trees and zipping. *Phys. Rev. Lett.*, 88, 048702.
[4] Bennett, C. H., Gacs, P., Li, M., Vitanyi, P. and Zurek, W. (1998) Information distance. *IEEE T. Inform. Theory*, 44, 1407-1423.
[5] Berbee, M. L. & Taylor, J. W. (1992) Two ascomycete classes based on fruiting-body characters and ribosomal DNA sequence. *Molecular Biology and Evolution* 9:278-284.
[6] Berman, P., Hannenhalli, S. and Karpinski, M. (2001). Approximation algorithm for sorting by reversals. Technical Report TR01-047, ECCC.
[7] Boore, J. L. and Brown, W. M. (1998) Big trees from little genomes: mithochondrial gene order as a phylogenetic tool. *Curr. Opin. Genet. Dev.*, 8, 668-674.
[8] Camin, J. and Sokal, R. (1965) A method for deducing branching sequences in phylogeny. *Evolution*, 19, 311-326.
[9] Cao, Y., Janke, A., Waddell, P. J., Westerman, M., Takenaka, O., Murata, S., Okada, N., Paabo, S. and Hasegawa, M. (1998) Conflict among individual mitochondrial proteins in resolving the phylogeny of eutherian orders. *J. Mol. Evol.*, 47, 307-322.
[10] Cao, Y., Okada, N. and Hasegawa, M. (1997) Phylogenetic position of guinea pigs revisited. *Mol. Biol. Evol.*, 14, 461%.
[11] Cavalli-Sforza, L. L. and Edwards, A. W. F. (1967) Phylogenetic analysis: models and estimation procedures. Evolution, 21, 550-570.
[12] Chen, X., Kwong, S. and Li, M (2000) A compression algorithm for DNA sequences and its applications in genome comparison. In Shamir, R., Miyano, S., Istrail, S., Pevzner, P. and Waterman, M. (eds) *Proceedings of the Fourth Annual International Conference on Computational Molecular Biology (RECOMB)*, ACM Press, Tokyo, Japan, pp. 107-117.
[13] Eck, R. V. and Dayhoff, M. O. (1966) *Atlas of Protein Sequence and Structure*, National Biomedical Research Foundation, Silver Spring, Md., pp. 161-202.
[14] Farach, M., Noordewier, M. O., Savari, S. A., Shepp, L. A., Wyner, A. D. and Ziv, J. (1995) On the entropy of DNA: Algorithms and measurements based on memory and rapid convergence. In *Symposium on Discrete Algorithms*, pp. 48-57.
[15] Felsenstein, J. (1973) Maximum likelihood and minimum-steps methods for estimating evolutionary trees from data on discrete characters. *Syst. Zool.*, 22, 240-249.
[16] Felsenstein, J. (1981) Evolutionary trees from DNA sequences: a maximum likelihood approach. *J. Mol. Evol.*, 17, 368-376.
[17] Felsenstein, J. (1989) PHYLIP (Phylogeny Inference Package). *Cladistics*, 5, 164-166.
[18] Felsenstein, J. and Churchill, G. A. (1996) A hidden Markov model approach to variation among sites in rate of evolution. *Mol. Bio. Evol.*, 13, 93-104.
[19] Fitch, W. M. (1971) Toward defining the course of evolution: minimum change for a specific tree topology. *Syst. Zool.*, 35, 406-416.
[20] Fitz-Gibbon, S. T. and House, C. H. (1999) Whole genome-based phylogenetic analysis of free-living microorganisms. *Nucleic Acids Res.*, 27, 4218-4222.
[21] Grumbach, S. and Tahi, F. (1993) Compression of DNA sequences. In *Data Compression Conference*, IEEE Computer Society Press, Sbowbird, Utah, USA.
[22] Grumbach, S. and Tahi, F. (1994) A new challenge for compression algorithms: genetic sequences. *J. Info. Proc. Man.*, 30, 875-866.
[23] Hannenhalli, S. and Pevzner, P. A. (1995) Towards a computational theory of genome rearrangements. *Lect. Notes Comput. Sci.*, 1000, 184-202.
[24] Hannenhalli, S. and Pevzner, P. A. (1999) Transforming cabbage into turnip: polynomial algorithm for sorting signed permutations by reversals. *JACM*, 46, 1-27.
[25] Henry, T., Iwen, P. C. & Hinrichs, S. H. (2000) Identification of Aspergillus species using internal transcribed spacer regions 1 and 2. *Journal of Clinical Microbiology* 38: 1510-1515.
[26] Herr, R. A., Tarcha, E. J., Taborda, P. R., Taylor, J. W., Ajello, L & Mendoza, L. (2001) Phylogenetic analysis of Lacazin lobol places this previously uncharacterized pathogen within the dimorphic *Onygenales. Journal of Clinical Microbiology* 39: 209-314.
[27] Huynen, M. A., Snel, B., III, W. L. and Bork, P. (2000) Predicting protein function by genomic context: quantitative evaluation and qualitative inferences. *Genome Res.*, 10, 1204-1210.
[28] Jukes, T. H. and Cantor, C. R. (1969) *Mammalian Protein Metabolism*, Academic Press, New York, pp. 21-132.
[29] Kececioglu, J. and Ravi, R. (1995) Of mice and men. Evolutionary distances. In *Proceedings of the 6th ACM-SIAM Symposium on Discrete Algorithms*, pp. 604-613.
[30] Kececioglu, J. and Ravi, R. (1998) Reconstructing a history of recombinations from a set of sequences. *Discrete Appl. Math.*, 88, 239-260.
[31] Kececioglu, J. and Sankoff, D. (1995) Exact and approximation algorithms for sorting by reversals, with application to genome rearrangement. *Algorithmica*, 13, 180-210.
[32] Kimura, M. (1980) A simple model for estimating evolutionary rates of base substitiutions through comparative studies of nucleotide sequences. *J. Mol. Evol.*, 16, 111-120.
[33] Kishino, H. and Hasegawa, M. (1989) Evolution of the maximum likelihood estimate of the evolutionary tree

[34] Lake, J. A. (1994) Reconstructing evolutionary trees from DNA and protein sequences: paralinear distances. *Proc. Natl Acad. Sci. USA,* 91, 1455-1459.

[35] Lanctot, J. K, Li, M. and Yang, E.-H. (2000) Estimating DNA sequence entropy. In *Symposium on Discrete Algorithms* pp. 409-418.

[36] Li, M., Badger, J. H., Chen, X., Kwong, S., Kearney, P. and Zhang, H. (2001) An information-based sequence distance and its application to whole mitochondrial genome phylogeny. *Bioinformatics,* 17, 149-154.

[37] Li, M. and Vitanyi, P. M. B. (1997) *An Introduction to Kolmogorov complexity and its Approximations,* 2nd edn. Springer-Verlag, New York.

[38] Lin, J. and Gerstein, M. (2000) Whole-genome trees based on the occurence of folds and orthologs: implications for comparing genomes on different levels. *Genome Res.,* 10, 808-818.

[39] Loewenstern, D. and Yianilos, P. N. (1999) Significantly lower entropy estimates for natural dna sequences. *J. Comput. Biol.,* 6. 125-142.

[40] Madsen, O., Scally, M., Douady, C. J., Kao, D. J., DeBry, R. W., Adkins, R., Amrine, H. M., Stanhope, M. J. de Jong, W. W. and Springer, M. S. (2001) Parallel adaptive radiations in two major clades of placental mammals. *Nature,* 409, 610-618.

[41] Milosavljevic, A. (1993) Discovering sequence similarity by the algorithmic significance. In *Intelligent Systems for Molecular Biology*, AAAI Press, Vienna, pp. 284-291.

[42] Murphy, W. J., Eizirik, E., O'brein, S. J., Madsen, O., Scally, M., Douady, C. J., Teeling, E., Ryder, O. A., Stanhope, M. J., de Jong, W. W. and Springer, M. S. (2001) Resolution of the early placental mammal radiation using bayesian phylogenetics. *Science,* 294, 2348-2351.

[43] Reyes, A., Gissi, C., Pesole, G., Catzeflis, F. M. and Saccone, C. (2000) Where do rodents fit? Evidence from the complete mitochondrial genome of Sciurus vulgaris. *Mol. Biol. Evol.,* 17, 979-983.

[44] Rivals, E., Dauchet, M., Delahaye, J.-P. and Delgrange, O. (1996) Compression and genetic sequences analysis. *Biochimie,* 78, 315-322.

[45] Rivals, E., Delgrange, O., Dauchet, M. and Delahaye, J. (1994) Compression and sequence comparison. In Apostolico, A. (ed.) DIMACS Workshop on Sequence Coniparison.

[46] Rivals, E., Delgrange, O., Delahaye, J. P., Dauchet, M., Delorme, M. O., Henaut, A. and Ollivier, E. (1997) Detection of significant patterns by compression algorithms: the case of approximate tandem repeats in DNA sequences. *Comput. Appl. Biosci,* 13, 131-136.

[47] Saitou, N. and Nei, M. (1987) The neighbor-joining method: a new method for reconstructing phylogenetic trees. Mol. Biol. Evol., 4, 406-425.

[48] Sankoff, D. (1999a) Geneome rearrangement with gene families. *Bioinformatics,* 15, 909-917.

[49] Sankoff,D. (1999b) Comparative mapping and genome rearrangement. In *From Jay Lush to Genomics: Visions For Animal Breeding and Genetics,* pp. 124-134.

[50] Sankoff, D. and Blanchette, M. (1998) Multiple genome rearrangement and breakpoint phylogeny. *J. Comput. Biol.,* 5, 555-570.

[51] Sankoff, D., Leduc, G., Antoine, N., Paquin, B., Lang, B. F. and Cedergen, R. (1992) Gene order comparisons for phylogenetic inference: Evolution of the mitochondrial genome. *Proc. Natl Acad Sci. USA,* 89, 6575-6579.

[52] Snel, B., Bork, P. and Huynen, M. A. (1999) Genome phylogeny based on gene content. *Nat. Genet.,* 21, 108-110.

[53] Snel, B., Bork, P. and Huynen, M. A. (2000) Genome evolution: gene fusion versus gene fission. *Trends Genet.,* 16, 9-11.

[54] Snel, B., Bork, P. and Huynen, M. A. (2002) Genomes in flux: the evolution of archaeal and proteobacterial gene content. *Genome Res.,* 12, 17-25.

[55] Tekaia, F., Lazcano, A. and Dujon, B. (1999) The genomic tree as revealed from whole proteome comparisons. *Genome Res.,* 9, 550-557.

[56] Thompson, J. D., Higgins, D. and Gibson, T. J. (1994) CLUSTAL W: improving the sensitivity of progressive multiple sequence alignment through sequence weighting, positions-specific gap penalties and weight matrix choice. *Nucleic Acids Res.,* 22, 4673-4680.

[57] Varre, J.-S., Delahaye, J.-P. and Rivals, E. (1999) Transformation distances: a family of dissimilarity measures based on movements of segments. *Bioinformatics,* 15, 194 202.

[58] Yokoyama, K., Biswas, S. K., Miyaji, M. & Hishlmura, K. (2000) Identification and phylogenetic relationship of the most common pathogenic relationship of the most common pathogenic Candida species inferred from mitochondrial cytochrome b gene sequences. *Journal of Clinical Microbiology* 38: 4503-4510.+

[59] Ziv, J. and Lempel, A. (1977) A universal algorithm for sequential data compression. *IEEE T. Inform. Theory,* 23, 337-343.

[60] Ziv, J. and Merhav, N. (1993) A measure of relative entropy between individual sequences with application to universal classification. *IEEE T. Inform. Theory,* 39, 1270-1279.

We claim:

1. A computer implemented method comprising:
   receiving a first nucleic acid sequence;
   generating a dictionary of words based on the first nucleic acid sequence such that the dictionary contains words that can be used to build the first nucleic acid sequence, the dictionary having a first number of words, each word having at least one nucleotide;
   receiving a first and second nucleotide of a second nucleic acid sequence, the second nucleotide being a nucleotide after the first nucleotide;
   combining said first and second nucleotide in sequence into a first set of nucleotides;
   at a computer, comparing the first set of nucleotides to the dictionary to determine whether the first set of nucleotides matches any word in the dictionary; and
   if the first set of nucleotides does not match any word in the dictionary, storing the first set of nucleotides as a new word in the dictionary.

2. The method of claim 1, wherein if the first set of nucleotides matches any word in the dictionary, receiving a third nucleotide of the second nucleic acid sequence, the third nucleotide being a nucleotide after the second nucleotide.

3. The method of claim 2, further comprising: combining the first set of nucleotides with the third nucleotide to make a second sequential set.

4. The method of claim 3, further comprising: comparing the second set of nucleotides to the dictionary to determine whether the second set of sequential nucleotides matches any word in the dictionary.

5. The method of claim 4, wherein if the second set of nucleotides does not match any word in the dictionary, storing said second set as a new word in the dictionary.

6. The method of claim 5, further comprising: determining the a second number of words in the dictionary after processing all the nucleotides in the second nucleic acid sequence.

7. The method of claim 6, further comprising: determining the difference between the second number and the first number.

8. The method of claim 7, further comprising: utilizing the difference to determine the distance between the first nucleic acid sequence and the second nucleic acid sequence.

9. A non-transitory computer readable medium comprising instructions that when executed by a machine, causes the machine to perform:
   identify a first nucleic acid sequence;
   generate a dictionary of words based on the first nucleic acid sequence such that the dictionary contains words that can be used to build the first nucleic acid sequence, the dictionary having a first number of words, each word having at least one nucleotide;
   receive a first and second nucleotide of a second nucleic acid sequence, the second nucleotide being a nucleotide after the first nucleotide;
   combine the first and second nucleotide in sequence into a first set of nucleotides;
   compare the first set of nucleotides to the dictionary to determine whether the first set of nucleotides matches any word in the dictionary; and
   if the first set of nucleotides does not match any word in the dictionary, store the first set of nucleotides as a new word in the dictionary.

10. A computer implemented method of creating a database of nucleotide units for a first nucleic acid sequence, the method comprising:
    receiving a first nucleotide of a first nucleic acid sequence;
    at a computer, determining whether the first nucleotide has been stored in a database in one or more storage devices as a unit for the first nucleic acid sequence, the unit being separate from the first nucleic acid sequence;
    if the first nucleotide has not been stored in the database separately from the first nucleic acid sequence, storing the first nucleotide as an individual unit for the first nucleic acid sequence, the unit being separate from the first nucleic acid sequence;
    if the first nucleotide has been stored in the database separately from the first nucleic acid sequence, receiving a second nucleotide of the first nucleic acid sequence, the second nucleotide being a nucleotide after the first nucleotide;
    combining the first and second nucleotides into a sequential set;
    at the computer, determining whether the sequential set has been stored in the database as a unit for the first nucleic acid sequence, the unit being separate from the first nucleic acid sequence; and
    if the sequential set has not been stored in the database separately from the first nucleic acid sequence, storing the sequential set as a unit in the database for the first nucleic acid sequence, the unit being separate from the first nucleic acid sequence.

11. The method of claim 10, wherein if the sequential set has been stored, receiving a third nucleotide of the first nucleic acid sequence, the third nucleotide being the next sequential nucleotide after the second nucleotide.

12. The method of claim 10, further comprising: determining the sum of all units stored for the first nucleic acid sequence.

13. A non-transitory computer readable medium comprising instructions that when executed by one or more machines causes the one or more machines to:
    receive a first nucleotide of a first nucleic acid sequence;
    determine whether the first nucleotide has been stored in a database in one or more storage devices as a unit for the first nucleic acid sequence, the unit being separate from the first nucleic acid sequence;
    if the first nucleotide has not been stored in the database separately from the first nucleic acid sequence, store the first nucleotide as an individual unit for the first nucleic acid sequence, the unit being separate from the first nucleic acid sequence;
    if the first nucleotide has been stored in the database separately from the first nucleic acid sequence, receive a second nucleotide of the first nucleic acid sequence, the second nucleotide being a nucleotide after the first nucleotide;
    combine the first and second nucleotides into a sequential set;
    determine whether the sequential set has been stored in the database as a unit for the first nucleic acid sequence, the unit being separate from the first nucleic acid sequence; and
    if the sequential set has not been stored in the database separately from the first nucleic acid sequence, store the sequential set as a unit in the database for the first nucleic acid sequence, the unit being separate from the first nucleic acid sequence.

14. A system for determining a distance between a first nucleic acid sequence and a second nucleic acid sequence, the system comprising one or more storage units and one or more data processors executing instructions to implement:
    receiving a first nucleic acid sequence;
    generating a dictionary of words based on the first nucleic acid sequence such that the dictionary contains words that can be used to build the first nucleic acid sequence, the dictionary having a first number of words, each word having at least one nucleotide;
    receiving a first and a second nucleotide of a second nucleic acid sequence, the second nucleotide being a nucleotide after the first nucleotide;
    combining said first and second nucleotide in sequence into a first set of nucleotides;
    comparing the first set of nucleotides to the dictionary to determine whether the first set of sequential nucleotides matches any word in the dictionary;
    storing said first set as a new word in the dictionary if the first set of nucleotides does not match any word in the dictionary.

15. The system of claim 14, wherein the system further implements receiving a third nucleotide of the second nucleic acid sequence if it is determined that the first set of nucleotides matches a word in the dictionary.

16. A computer-implemented method of determining the distance between two nucleic acid sequences, the method comprising:
    determining the number of words in a first nucleic acid sequence;
    combining the first sequence with a second nucleic acid sequence to make a combined nucleic acid sequence;
    determining the number of words in the combined nucleic acid sequence; and
    determining, at one or more computers, a number representing the difference between the number of words in the combined nucleic acid sequence and the first nucleic acid sequence to determine the distance between the first nucleic acid sequence and the second nucleic acid sequence.

17. A non-transitory computer readable medium comprising instructions that when executed by one or more computers cause the one or more computers to:
   determine the number of words in a first nucleic acid sequence;
   combine the first sequence with a second nucleic acid sequence to make a combined nucleic acid sequence;
   determine the number of words in the combined nucleic acid sequence; and
   determine the difference between the number of words in the combined nucleic acid sequence and the first nucleic acid sequence to determine a distance between the first nucleic acid sequence and the second nucleic acid sequence.

18. A computer implemented method of determining a distance between a first nucleic acid sequence and a second nucleic acid sequence, the method comprising:
   determining a first number representing the number of words in a first dictionary that can be used to build a first nucleic acid sequence, each word comprising at least one nucleotide;
   determining a second number representing the number of words in a second dictionary that can be used to build a second nucleic acid sequence;
   determining a third number representing the number of words in a third dictionary that can be used to build a first combined nucleic acid sequence comprising the second nucleic acid sequence appended to the first nucleic acid sequence;
   determining a fourth number representing the number of words in a fourth dictionary that can be used to build a second combined nucleic acid sequence comprising the first nucleic acid sequence appended to the second nucleic acid sequence; and
   determining, at one or more computers, a distance between the first and second nucleic acid sequences based on the first number, the second number, the third number, and the fourth number.

19. The method of claim 18, comprising in which determining a distance between the first and second nucleic acid sequences comprises determining the distance between the first and second nucleic acid sequences based on a distance measure for nucleic acid sequences that satisfies the triangle inequality, such that a distance between the first and second nucleic acid sequences is no greater than a sum of a first distance between the first nucleic acid sequence and a third nucleic acid sequence, and a second distance between the second and third nucleic acid sequences.

20. The method of claim 18, comprising:
   determining a first difference between the third number and the first number;
   determining a second difference between the fourth number and the second number; and
   determining the distance between the first and second nucleic acid sequences based on a maximum of the first difference and the second difference.

21. The method of claim 20, comprising determining a normalized distance between the first and second nucleic acid sequences based on the maximum of the first difference and the second difference, divided by a maximum of the first number and the second number.

22. The method of claim 18, comprising
   determining a first difference between the third number and the first number;
   determining a second difference between the fourth number and the second number; and
   determining the distance between the first and second nucleic acid sequences based on a sum of the first difference and the second difference.

23. The method of claim 22, comprising determining a normalized distance based on the sum of the first difference and the second difference, the sum being divided by the third number.

24. The method of claim 22, comprising determining a normalized distance based on the sum of the first difference and the second difference, the sum being divided by an average of the third number and the fourth number.

25. The method of claim 18 in which generating the first dictionary comprises:
   receiving a first and second nucleotide of the first nucleic acid sequence, the second nucleotide being after the first nucleotide in the first nucleic acid sequence;
   combining the first and second nucleotides in sequence into a first set of nucleotides; and
   adding the first set of nucleotides as a word into the first dictionary if the first set of nucleotides is not already in the first dictionary.

26. The method of claim 25 in which if the first set of nucleotides is already in the first dictionary, receiving a third nucleotide of the first nucleic acid sequence, the third nucleotide being after the second nucleotide,
   combining the first set of nucleotides with the third nucleotide to make a second set of nucleotides, and
   adding the second set of nucleotides as a word into the first dictionary if the second set of nucleotides is not already in the first dictionary.

* * * * *

UNITED STATES PATENT AND TRADEMARK OFFICE
CERTIFICATE OF CORRECTION

PATENT NO. : 8,725,419 B2  
APPLICATION NO. : 10/561889  
DATED : May 13, 2014  
INVENTOR(S) : Sayood et al.

Page 1 of 1

It is certified that error appears in the above-identified patent and that said Letters Patent is hereby corrected as shown below:

On the title page, column 1, Item [75], please delete "Linclon" and insert -- Lincoln --, therefor.

On the title page, column 1, line 12 Item [56], please delete "Delection" and insert -- Deletion --, therefor.

On the title page, column 2, line 15 Item [56], please delete "Curro" and insert -- Curr --, therefor.

On title page 2, column 2, line 57 Item [56], please delete "Infonn" and insert -- Inform --, therefor.

In the Claims

Column 25, line 2 (Claim 6), please delete "the a" and insert -- the --, therefor.

Column 27, line 42 (Claim 19), after "claim 18," delete "comprising.".

Signed and Sealed this  
Seventh Day of October, 2014

Michelle K. Lee  
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,725,419 B2 |
| APPLICATION NO. | : 10/561889 |
| DATED | : May 13, 2014 |
| INVENTOR(S) | : Sayood et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2174 days.

Signed and Sealed this
Twenty-first Day of July, 2015

Michelle K. Lee
*Director of the United States Patent and Trademark Office*